United States Patent [19]

Gross

[11] Patent Number: 5,356,787

[45] Date of Patent: Oct. 18, 1994

[54] METHOD OF IDENTIFYING COMPOUNDS THAT MODULATE MYOCARDIAL CALCIUM-INDEPENDENT PHOSPHOLIPASE $A_2$ ACTIVITY

[75] Inventor: Richard Gross, St. Louis, Mo.

[73] Assignee: Washington University, St. Louis, Mo.

[21] Appl. No.: 53,616

[22] Filed: Apr. 23, 1993

[51] Int. Cl.$^5$ .................. C12Q 1/34; G01N 23/00
[52] U.S. Cl. .......................... 435/18; 435/4; 435/35; 435/194; 435/195; 435/968; 436/55; 436/57; 436/63; 436/804; 424/94.2; 424/94.6; 424/1.77; 424/1.81
[58] Field of Search ................. 435/18, 4, 35, 21, 194, 435/195, 968; 436/55, 57, 63, 804; 424/1.1, 94.2, 94.6

[56] References Cited

PUBLICATIONS

Hazen et al, The Journal of Biological Chemistry, vol. 265, No. 18, Jun. 25, pp. 10622–10630, 1990.
Hazen et al, The Journal of Biological Chemistry, vol. 266, No. 22, Aug. 5, pp. 14526–14534, 1991.
Berg et al., "Interfacial Catalysis by Phospholipase $A_2$: Determination of the Interfacial Kinetic Rate Constants," Biochem, 30:7283–7297, 1991.
Bills et al., "Selective Release of Archidonic Acid from the Phospholipids of Human Platelets in Response to Thrombin," J. Clin. Invest., 60:1–6, 1977.
Clark et al., "A Novel Arachidonic Acid–Selective Cytosolic PLA$_2$ Contains a Ca$^{2+}$–Dependent Translocation Comain with Homology to PKC and GAP," Cell, 65:1043–1051, 1991.
Dennis, E. A., "Phospholipases," Enzymes 3rd Ed., 16:307–353, 1983.
Emerk et al., "Rabbit Muscle Phosphofructokinase: The Effect of the State of the Enzyme and Assay Procedure on the Kinetic Properties," Arch. of Biochem. Biophys., 168:210–218, 1975.
Ford et al., "Differential Accumulation of Diacyl and Plasmalogenic Diglycerides During Myocardial Ischemia," Circ. Res., 64:173–177, 1989.
Gassama–Diagne et al., "Purification of a New, Calcium–independent, High Molecular Weight Phospholipase $A_2$/Lysophospholipase (Phospholipase B) from Guinea Pig Intestinal Brush–border Membrane," J. Biol. Chem., 264:9470–9475, 1989.
Ghomashchi et al., "Interfacial Catalysis by Phospholipase $A_2$: Substrate Specificity in Vesicles," Biochem, 30:7318–7329, 1991.
Ghomashchi et al., "Kinetic Analysis of a High Molecular Weight Phospholipase $A_2$ from Rat Kidney: Divalent Metal–Dependent Trapping of Enzyme on Product–Containing Vesicles," Biochem, 31:3814–3824, 1992.
Gross, R. W., "Myocardial Phospholipases $A_2$ and Their Membrand Substrates," Trends in Cardiovascular Medicine, 2:115–121, 1992.
Han et al., "Semisynthesis and Purification of Homogeneous Plasmenylcholine Molecular Species," Anal. Biochem., 200:119–124, 1992.
Hazen et al., "Purification and Characterization of Canine Myocardial Cytosolic Phospholipase $A_2$," J. Biol. Chem., 265:10622–10630, 1990.

(List continued on next page.)

Primary Examiner—Michael G. Wityshyn
Assistant Examiner—Abdel A. Mohamed
Attorney, Agent, or Firm—Woodcock Washburn Kurtz Mackiewicz & Norris

[57] ABSTRACT

A method of identifying compounds that modulate the activity of myocardial calcium-independent phospholipase $A_2$ is disclosed. In a test assay of the method of the invention, myocardial calcium-independent phospholipase $A_2$ 40kDa catalytic subunit, 85kDa phosphofructokinase isoform, ATP, a substrate and a test compound are combined and the myocardial calcium-independent phospholipase $A_2$ activity is determined. The level of activity observed in the test assay is compared to the level of activity generated from a control assay which is similar to the test assay but which does not include the test compound. Essentially pure myocardial calcium-independent phospholipase $A_2$ 85kDa phosphofructokinase isoform is also disclosed.

23 Claims, 8 Drawing Sheets

PUBLICATIONS

Hazen et al., "ATP-dependent Regulation of Rabbit Myocardial Cytosolic Calcium-independent Phospholipase $A_2$," *J. Biol. Chem.*, 266:14526–14534, 1991.

Hazen et al., "Human myocardial cytosolic $Ca^{2+}$-independent phospholipase $A_2$ is modulated by ATP," *Biochem. J.*, 280:581–587, 1991.

Hazen et al., "Purification and Characterization of Cytosolic Phospholipase $A_2$ Activities from Canine Myocardium and Sheep Platelets," *Methods in Enzymology*, 197:400–411, 1991.

Hemler et al., "Evidence for a Peroxide-initiated Free Radical Mechanism of Prostaglandin Biosynthesis," *J. Biol. Chem.*, 255:6253–61, 1980.

Husebye et al., "Characterization of Phospholipase Activities in Chromaffin Granule Ghosts Isolated from the Bovine Adrenal Medulla," *Biochem. Biophys. Acta*, 920:120–130, 1987.

Jain et al., "Interfacial Catalysis by Phospholipase $A_2$: Dissociation Constants for Calcium, Substrate, Products, and Competitive Inhibitors," *Biochem*, 30:7306–7317, 1991.

Jain et al., "Interfacial Catalysis by Phospholipase $A_2$: Monomeric Enzyme is ully Catalytically Active at the Bilayer Interface," *Biochem*, 30:7330–7340, 1991.

Jensenius et al., "Eggs: Conveniently Packaged Antibodies. Methods for Purification of Yolk IgG," *J. Immunol. Methods*, 46:63–68, 1981.

Kramer et al., "The $Ca^{2+}$-sensitive Cytosolic Phospolipase $A_2$ Is a 100-kDa Protein in Human Monoblast U937 Cells," *J. Biol. Chem.*, 266:5268–5272, 1991.

Lands, W. E. M., "Biological Consequences of Fatty Acid Oxygenase Reaction Mechanisms," *Prostaglandins Leukotrienes Med.*, 13:35–46, 1984.

Loeb et al., "Identification and Purification of Sheep Platelet Phospholipase $A_2$ Isoforms", *J. Biol. Chem.*, 261:10467–10470, 1986.

Leslie et al., "Properties and Purification of an Arachidonoyl-Hydrolyzing Phospholipase $A_2$ from a Macrophage Cell Line, RAW 264.7," *Biochem. Biophys. Acta*, 963:476–492, 1988.

Mizuno et al., "Effects of Non-Steroidal Anti-Inflammatory Drugs on Fatty Acid Cyclooxygenase and Prostaglandin Hydroperoxidase Activities," *Prostaglandins*, 23:743–57, 1982.

Needleman et al., "Arachidonic Acid Metabolism," *Annu. Rev. Biochem.*, 55:69–102, 1986.

Nijssen et al., "Identification of a Calcium-Independent Phospholipase $A_2$ in a Rat Lung Cytosol and Differentiation from Acetylhydrolase for 1-alkyl-2-acetyl-sn-glycero-3-phosphocholine (PAF-acether)," *Biochem. Biophys. Acta*, 876:611–618, 1986.

Pierik et al., "Calcium-Independent Phospholipase $A_2$ in Rat Tissue Cytosols," *Biochem. Biophys. Acta*, 962:345–353, 1988.

Ramadoss et al., "Affinity Chromatography of Phosphofructokinase," *Arch. Biochem. Biophys.*, 175:487–484, 1976.

Ross et al., "Phospholipase Activities of the $P388D_1$ Macrophage-like Cell Line," *Arch. Biochem. Biophys.*, 238:247–258, 1985.

Samuelson et al., "Prostaglandins and Thromboxanes," *Annu. Rev. Biochem.*, 47:997–1029, 1978.

Van den Bosch, H., "Intracellular Phospolipases A," *Biochem. Biophys. Acta.*, 604:191–246, 1980.

Verheij, et al., "Structure and Function of Phospholiphase $A_2$," *Rev. Physiol. Biochem. Exp. Pharmacol*, 91:92–203, 1981.

Wolf et al., "Identification of Neutral Active Phospholipase C Which Hydrolyzes Choline Glycerophospholipids and Plasmalogen Selective Phospholipase $A_2$ in canine Myocardium," *J. Biol. Chem.*, 260:7295–7303, 1985.

Zupan et al., "Cloning and Expression of a Human 14-3-3 Protein Mediating Phospholipolysis," *J. Biol. Chem.*, 267:8707–8710, 1992.

Zupan et al., "Calcium is Sufficient But Not Necessary for Activation of Sheep Platelet Cytosolic Phospholipase $A_2$," *FEBS*, 284:27–30, 1991.

SEQUENCE LISTING (1) GENERAL INFORMATION:

(iii) NUMBER OF SEQUENCES: 4

(2) INFORMATION FOR SEQ ID NO:1:

(i) SEQUENCE CHARACTERISTICS:
        (A) LENGTH: 18 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO:1:

```
Ile Ala Val Leu Thr Gln Gln Gly Asp Ala Gln Gly Met Asn Ala Ala
1               5                   10                  15

Val Arg
```

(2) INFORMATION FOR SEQ ID NO:2:

(i) SEQUENCE CHARACTERISTICS:
        (A) LENGTH: 18 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO:2:

```
Ile Ala Val Leu Thr Ser Gly Gly Asp Ala Gln Gly Met Asn Ala Ala
1               5                   10                  15

Val Arg
```

(2) INFORMATION FOR SEQ ID NO:3:

(i) SEQUENCE CHARACTERISTICS:
        (A) LENGTH: 16 amino acids
        (B) TYPE: amino acid
        (D) TOPOLOGY: linear (ii) MOLECULE TYPE: peptide (v) FRAGMENT TYPE: internal (xi) SEQUENCE DESCRIPTION: SEQ ID NO:3:

```
Val Leu Gly His Met Ser Gly Gly Cys Ser Pro Thr Pro Phe Asp Arg
1               5                   10                  15
```

(2) INFORMATION FOR SEQ ID NO:4:

(i) SEQUENCE CHARACTERISTICS:
        (A) LENGTH: 16 amino acids
        (B) TYPE: amino acid
        (D) TOPOLOGY: linear (ii) MOLECULE TYPE: protein (v) FRAGMENT TYPE: internal (xi) SEQUENCE DESCRIPTION: SEQ ID NO:4:

```
Val  Leu  Gly  His  Met  Gln  Gln  Gly  Gly  Ser  Pro  Thr  Pro  Phe  Asp  Arg
 1              5                        10                       15
```

METHOD OF IDENTIFYING COMPOUNDS THAT MODULATE MYOCARDIAL CALCIUM-INDEPENDENT PHOSPHOLIPASE A$_2$ ACTIVITY

ACKNOWLEDGEMENT OF GOVERNMENT SUPPORT

This invention was made with government support under HL 34839 awarded by NIH. The government has certain rights in the invention.

FIELD OF THE INVENTION

The present invention relates to methods of identifying compounds that modulate myocardial calcium-independent phospholipase A$_2$ activity. The present invention provides assay components which may be combined to assess the effect that a test compound has on phospholipase activity.

BACKGROUND OF THE INVENTION

Since the enzymes in eicosanoid oxidative cascades exclusively utilize free (i.e., non-esterified) arachidonic acid and the cellular content of non-esterified arachidonic acid in resting cells is exceedingly low (See: Samuelsson, B., et al. (1978) *Annu. Rev. Biochem.* 47:997–1029; Bills, T. K., et al. (1977) *J. Clin. Invest.* 60:1–6; Lands, W. E. M. (1984) *Prostaglandins Leukotrienes Med.* 13:35–46; Hemler M. E. and W. E. M. Lands (1980) *J. Biol. Chem.* 255:6253–61; Mizxuno, K., et al. (1982) *Prostaglandins* 23:743–57; and Needleman, P., et al. (1986) *Annu. Rev. Biochem.* 55:69–102), it seems evident that the activation of phospholipases A$_2$ represents an enabling event in the generation of eicosanoid-based lipid second messengers. The release of arachidonic acid and the concomitant accumulation of amphiphilic reaction products modulate cellular responses to a wide variety of physiologic and pathophysiologic perturbations. The precise complement of downstream enzymes which determine the metabolic fate of released arachidonic acid is modulated by each cell's genetic program and by alterations in the physical and chemical environment of the activated cell. Thus, dynamic alterations in intracellular phospholipase A$_2$ activity represent the critical step in the initiation of eicosanoid-based signaling cascades while the chemical interpretation of the signal reflects both the distant and proximal history of the activated cell.

Despite the importance of alterations in the activity of intracellular phospholipases in both physiologic and pathophysiologic processes, the precise identification of the biochemical mechanisms which regulate the activity of these enzymes has remained elusive. Although initial studies on the regulation of phospholipases A$_2$ have focused in large part on the direct role of calcium ion in the activation of phospholipases A$_2$ (See: Verheij, N. M., et al., (1981) *Rev. Physiol. Biochem. Pharmacol.* 91: 91–203; van den Bosch, H. (1980) *Biochim. Biophys. Acta.* 604: 191–246; Dennis, E. A. (1983) *Enzymes* 3rd Ed. 307–353; Dennis, E. A. (1983) *Prostaglandins, In the Enzymes* P. D. Boyer, ed. (Academic: New York) 16:307–354; and Loeb, L. A. and R. W. Gross (1986) *J. Biol. Chem.* 261:10467–10470), it has recently become evident that additional biochemical mechanisms play essential roles in the regulation of intracellular phospholipases A$_2$ (See: Zupan, L. A., et al., (1991) *FEBS* 284:27–30; Ghomashchi, F., et al. (1992) *Biochem* 31:3814–3824; Berg, O. G., et al. (1991) *Biochem.* 30:7283–7297; Jain, M. K., et al. (1991) *Biochem.* 30:7306–7317; and Jain, M. K., et al. (1991) *Biochem.* 30:7306–7340) . This was perhaps best exemplified by the identification of calcium-independent phospholipases A$_2$ in a variety of cell types which manifest full catalytic activity and substrate affinity in the absence of calcium ion (.See: Wolf, R. A. and R. W. Gross (1985) *J. Biol. Chem.* 260:7295–7303; Hazen, S. L., et al., (1990) *J. Biol. Chem.* 265:10622–10630; Ross, M. I., et al., (1985) *Arch. Biochem. Biophys.* 238:247–258; Nijssen, J. G. et al., (1986) *Biochim. Biophys. Acta* 876:611–618; Husebye, E. S., and T. Flatmark (1987) *Biochim. Biophys. Acta* 920:120–130; Pierik, A. J., et al., (1988) *Biochim. Biophys. Acta* 962:345–353; and Gassama-Diagne A., et al., (1989) *J. Biol. Chem.* 264:9470–9475).

The recent demonstration that alterations in ATP concentration influence the activity and longevity of myocardial cytosolic calcium-independent phospholipase A$_2$ and that myocardial cytosolic phospholipase A$_2$ exists as a high molecular weight catalytic complex comprised of catalytic and regulatory polypeptides have provided initial insight into the importance of ligand modulated protein-protein interactions in the regulation of this class of enzymes.

Myocardial cytosolic calcium-independent phospholipase A$_2$ has been reported to exist as a 400 kDa cytosolic complex that exhibits MCPA$_2$ activity and can be purified from rabbit myocardial muscle tissue. In addition, MCPA$_2$ activity was observed in the purified 40 kDa catalytic subunit of MCPA$_2$ which has been shown to be active in a calcium-independent/ATP regulated manner in vitro (Hazen, S. L., and R. W. Gross (1991) *J. Biol. Chem.* 266:14526–14534).

The catalytic subunit of MCPA$_2$ has been identified to be a 40 kDa protein which is considered unstable and is not regulated by ATP. Following the initial description (Wolf, R. A. and Gross, R. W. (1985) *J. Biol. Chem.* 260:7295–7303; Loeb, L. A. and Gross, R. W. (1986) *J. Biol. Chem.* 261:10467–10470), characterization (Kramer, R. M., et al. (1991) *J. Biol. Chem* 266:5268-5272; Leslie, C. C. , et al. (1988) *Biochem. Biophys. Acta* 963:476–492 and Hazen, S. L., et al. (1990) *J. Biol. Chem.* 265:10622–10630) and, in some cases, molecular cloning (Clark, J. D., et al (1991) *Cell* 65:1043–1051 and Zupan, L. A et al. (1992) *J. Biol. Chem.* 267:8707–8710) of intracellular phospholipases A$_2$, attention has focused on the biochemical mechanisms responsible for their regulation.

Recent studies have demonstrated that myocardial cytosolic calcium-independent phospholipase A$_2$ catalytic activity is regulated by protein-protein interactions which are modulated by ATP (Hazen, S. L. and Gross, R. W. (1991) *J. Biol. Chem.* 266:14526–14534). The 400 kDa complex that has been identified to contain MCPA$_2$ activity is relatively stable and regulated by ATP.

Since activation of myocardial cytosolic calcium-independent phospholipase A$_2$ has been implicated in the genesis of electrophysiologic dysfunction and myocytic cellular necrosis during myocardial ischemia Gross, R. W., (1992) *Trends in Cardiovascular Medicine* 2:115–121, the chemical identity of the elements responsible for the modulation of calcium-independent phospholipase A$_2$ and the nature of the molecular mechanism through which ATP modulates the interactions between the catalytic and regulatory polypeptides have attracted considerable attention.

There is a need for a method of identifying compounds which modulate the activity of phospholipase $A_2$. Such compounds would be useful to influence intracellular phospholipase activity involved in both physiologic and pathophysiologic processes and thereby affect those processes.

SUMMARY OF THE INVENTION

The present invention relates to a method of identifying compounds that modulate the activity of myocardial calcium-independent phospholipase $A_2$. The present invention comprises the steps entailed in performing a test assay and comparing the results observed in the test assay with the results of a control assay, In the test assay of the method of the invention, myocardial calcium-independent phospholipase $A_2$ 40kDa catalytic subunit, 85kDa phosphofructokinase isoform, ATP, a substrate and a test compound are combined and the myocardial calcium-independent phospholipase $A_2$ activity is determined. The level of activity observed in the test assay is compared to the level of activity generated from a control assay which is similar to the test assay but which does not include the test compound.

The present invention relates to an essentially pure myocardial calcium-independent phospholipase $A_2$ and an essentially pure $MCPA^2$ regulatory subunit which is an 85kDa phosphofructokinase isoform.

DETAILED DESCRIPTION OF THE INVENTION

Figure 1:
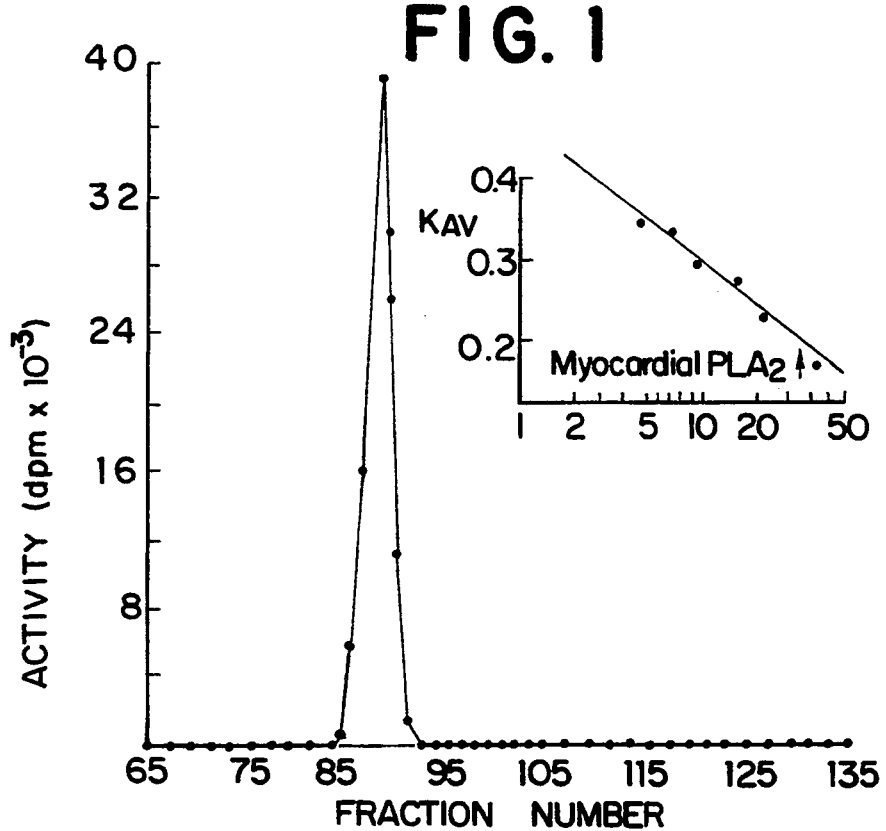
FIG. 1 illustrates the results of gel filtration chromatography of human myocardial cytosolic calcium-independent phospholipase $A_2$ activity.

To further the understanding of the molecular mechanisms which regulate calcium-independent phospholipase $A_2$, the specific factor which, in combination with the myocardial calcium-independent phospholipase $A_2$ (MCPA$_2$) 40 kDa catalytic subunit, is involved in MCPA$_2$ activity was identified and characterized. The identification and characterization of the components that are involved in the myocardial calcium-independent phospholipase $A_2$ reaction allow for the design of an assay useful in the discovery of compounds which affect myocardial calcium-independent phospholipase $A_2$ activity.

According to the invention, an active calcium-independent phospholipase $A_2$ complex consisting of a 40 kDa catalytic subunit associated with four molecules of an 85 kDa phosphofructokinase (PFK) isoform which represents a tetrameric regulatory element, is combined with ATP, a substrate and a test compound to examine the effect that the test compound has on the phospholipase reaction. As a control, the assay can be performed without the test compound.

The present invention arises from the discovery that the MCPA$_2$ associates with a phosphofructokinase (PFK) isoform to form an ATP-regulated complex that has phospholipase activity. This discovery allows for the identification of molecules that modulate the activity of MCPA$_2$. It has been determined that an 85 kDa PFK isoform associates with the 40 kDa MCPA$_2$ catalytic polypeptide, potentially regulating MCPA$_2$ catalytic activity. The PFK isoform associates with the MCPA$_2$ catalytic subunit at a ratio of 4 to 1. Thus, four PFK isomer molecules combine with a single catalytic subunit molecule to form an active complex.

According to the invention, compounds are identified which modulate MCPA$_2$ activity. A screen has been designed which compares the cleavage of a phospholipid substrate by a combination of components which include MCPA$_2$ catalytic subunit, PFK isoform regulatory subunits and ATP in the presence or absence of test compounds. Using this screen, compounds can be identified which affect MCPA$_2$ activity. By identifying molecules which can affect the activity of MCPA$_2$, the release of arachidonic acid can be effected. By controlling the release of arachidonic acid, the generation of eicosanoid-based lipid second-messengers can be effected. In particular, compounds can be identified which inhibit or eliminate the MCPA$_2$ activity. Such compounds may be useful as therapeutics for treatment of arthritis, and ischemic syndromes such as myocardial, cerebral and renal infarctions, transplant rejection, inflammation, atherosclerosis, diabetes and hypertension.

The method of the present invention comprises the steps of first combining 40 kDa catalytic subunit, 85 kDa tetrameric PFK isoform, ATP, a phospholipase substrate and a test compound. The mixture is maintained for a sufficient time to allow phospholipase processing of the substrate; that is, to allow the enzyme to remove an acyl linkage from the substrate. After such time, the level of phospholipase activity is measured by either measuring the amount of substrate which has not been processed or by measuring the amount of either reaction product present. This amount is compared with the level of phospholipase activity resulting from a control assay performed without the test compound.

Generally, the level of phospholipase activity is measured by determining the amount of substrate that has been processed. This is performed most preferably by using substrate that contains a labelled phosphorous atom which can be cleaved by the phospholipase. After allowing time for the reaction to occur, the substrate is isolated and the level of labelled substrate remaining is indicative of the level of phospholipase reaction. The sn-2 chain is most preferably radiolabelled. Other means of measuring processed or unprocessed substrate are contemplated and can be readily performed by those having ordinary skill in the art.

The 40 kDa $MCPA_2$ catalytic subunit and the 85 kDa PFK isoform can be purified from myocardial tissue as a 400 kDa complex. However, obtaining the complex from natural sources is impractical to meet the quantity requirements of a high volume screening effort. Accordingly, the 40 kDa $MCPA_2$ catalytic subunit and the 85 kDa PFK isoform can be purified or produced separately and combined to form the active complex in vitro. Thus, either of two protocols may be followed: a first protocol in which the $MCPA_2$ is provided as a purified complex that is isolated from tissue, or a second protocol in which the $MCPA_2$ catalytic subunit and PFK isoform are produced separately and reconstituted in vitro to form an active complex.

Substrates useful in the methods of the present invention include any compounds that can be converted by the hydrolytic cleavage or acyl transfer similar to that employed by the phospholipase reaction. Preferred substrates include plasmenylcholine, plasmenylethanolamine, diacylphospholipids, alkylphospholipids and other lipid substrates containing the appropriate functionality including non-polar substrates such as, for example, triglycerides, diglycerides and monoglycerides. Substrates useful to practive the methods of the present invention will be readily apparent to those having ordinary skill in the art. The more preferred substrate is plasmenylcholine. It is most preferred that the substrate is plasmenylcholine labelled at the sn-2 acyl chain.

$MCPA_2$ may be isolated from tissue as a complex by performing, for example, the following procedure employed for purification of rabbit myocardial cytosolic calciumindependent phospholipase $A_2$. New Zealand White rabbits are sacrificed, and hearts are rapidly removed and perfused retrograde (60 mmHg) for ten minutes with modified Krebs-Henseleit buffer utilizing a Langendorf perfused heart model (Ford, D. A., et al. (1989) Circ. Res. 64:173-177). Ventricular tissue is subsequently isolated, weighed, and placed in 0° C. homogenization buffer (0.25M sucrose (grade 1), 10 mM imidazole, 10 mMKCl pH 7.8) at 25% (w/v). Myocardium is minced utilizing sharp scissors, homogenized utilizing a Potter-Elvehjem apparatus, and cytosol is subsequently prepared by differential centrifugation as previously described (Hazen, S. L., et al., (1990) J. Biol. Chem. 265:10622-10630). Cytosol is routinely dialyzed against two changes of 500 volumes of homogenization buffer (8 h/dialysis) and either utilized directly or stored in liquid nitrogen as individual aliquots for up to three months.

In the protocol using a complex purified from tissue:

The reaction mixture can contain substrate at a final concentration of 0.1 nM-500 $\mu$M, preferably 10$\mu$M.

The amount of 400 kDa complex used can be 1 pg-1 mg, preferably 1 $\mu$g.

ATP is commercially available from Sigma. The reaction mixture can contain ATP at a final concentration of 0.1 $\mu$M-100 $\mu$M.

The reaction mixture can contain test compound at a final concentration 1 pM-100 $\mu$M, preferably 1 $\mu$M.

The preferred assay buffer is (final conditions) 100 mM Tris, 4 mM EGTA, 4 mM EDTA, pH 7.0.

The reaction can take place from about 10 seconds to about 30 minutes at about 5° C. to about 37° C. The preferred conditions are 37° C. for 1 minute.

After reaction time has elapsed, the reaction may be terminated by addition of a compound or solution. The preferred method of stopping the reaction is by quenching the reaction solution with butanol.

Alternatively, the catalytic and regulatory subunits may be produced or isolated separately and combined as part of the reaction assay.

The catalytic subunit may be isolated from natural material or produced using recombinant methods. To purify the 40 kDa catalytic subunit from natural material, the cytosolic complex is partially purified as described above. Phospholipase $A_2$ from perfused rabbit myocardium is further purified by sequential ion exchange, chromatofocusing, ATP affinity and Mono-Q chromatographies employing methods similar to those described previously for canine myocardial cytosolic phospholipase $A_2$ (Hazen, S. L., et al., (1990) J. Biolo Chem. 265:10622-10630). For reconstitution experiments, either the ATP affinity column eluent (specific activity=21 $\mu$mol/mg·min; 13,500-fold purified) or the Mono-Q fast protein liquid chromatography eluent (specific activity=59 $\mu$mol/mg·min; 37,800-fold purified) is utilized. The purity of the Mono-Q eluent is corroborated by $^{125}$I-autoradiography of SDS-PAGE[1] gels of Bolton Hunter $^{125}$I-labeled proteins which demonstrate a predominant band at 40 kDa. Alternatively, the protein may be produced using recombinant DNA technology whereby an expression vector which comprises a DNA sequence that encodes the protein is inserted into a host cell. The protein may, by these methods, be produced in large quantities and purified by standard techniques.

The regulatory subunit may be isolated from natural material or produced using recombinant methods. To purify the 85 kDa regulatory subunit from natural material, a number of methods can be utilized including, but not limited to, those described herein. Alternatively, the protein may be produced using recombinant DNA technology whereby an expression vector which comprises a DNA sequence that encodes the protein is inserted into a host cell. The protein may, by these methods, be produced in large quantities and purified by standard techniques.

The 85 kDa PFK isoform may be produced by routine means using readily available starting materials as described above. The nucleic acid sequence encoding the 85 kDa PFK isoform as well as the amino acid sequence of the protein can be determined by those having ordinary skill in the art following the teachings provided herein.

Provision of a suitable DNA sequence encoding the desired protein permits the production of the protein using recombinant techniques now known in the art. The coding sequence can be obtained, for example, by retrieving the DNA sequence from a cDNA library using probes based upon sequence information disclosed herein or from a cDNA expression library using antibodies that bind to the protein. Once the DNA sequence has been elucidated, a DNA molecule having that sequence can be prepared chemically using a synthesized nucleotide sequence. When the coding DNA is prepared synthetically, advantage can be taken of known codon preferences of the intended host where the DNA is to be expressed.

One having ordinary skill in the art can, following the teachings described herein and using well known techniques, obtain a DNA molecule encoding the 85 kDa PFK isoform protein and insert that DNA molecule into a commercially available expression vector for use in well known expression systems. For example, the commercially available plasmid pSE420 (Invitrogen, San Diego, Calif.) may be used for production in *E. coli*. The commercially available plasmid pYES2 (Invitrogen, San Diego, Calif.) may be used for production in *S. cerevisiae* strains of yeast. The commerically available MaxBac ™ (Invitrogen, San Diego, Calif.) complete bacculovirus expression system may be used for production in insect cells. The commercially available plasmid pcDNA I (Invitrogen, San Diego, Calif.) may be used for production in may be used for production in mammalian cells such as Chinese Hamster Ovary cells. One having ordinary skill in the art can use these commercial expression vectors and systems or others to produce 85 kDa PFK isoform protein using routine techniques and readily available starting materials.

One having ordinary skill in the art may use other commercially available expression vectors and systems or produce vectors using well known methods and readily available starting materials. Expression systems containing the requisite control sequences, such as promoters and polyadenylation signals, and preferably enhancers, are readily available and known in the art for a variety of hosts (See e.g., Sambrook et al., (1989) *Molecular Cloning a Laboratory Manual*, Second Ed. Cold Spring Harbor Press). Thus, the desired proteins can be prepared in both prokaryotic and eukaryotic systems, resulting in a spectrum of processed forms of the protein.

The most commonly used prokaryotic system remains *E. coli*, although other systems such as *B. subtilis* and *Pseudomonas* are also useful. Suitable control sequences for prokaryotic systems include both constitutive and inducible promoters including the lac promoter, the trp promoter, hybrid promoters such as tac promoter, the lambda phage P1 promoter. In general, foreign proteins may be produced in these hosts either as fusion or mature proteins. When the desired sequences are produced as mature proteins, the sequence produced may be preceded by a methionine which is not necessarily efficiently removed. Accordingly, the peptides and proteins claimed herein may be preceded by an N-terminal Met when produced in bacteria. Moreover, constructs may be made wherein the coding sequence for the peptide is preceded by an operable signal peptide which results in the secretion of the protein. When produced in prokaryotic hosts in this matter, the signal sequence is removed upon secretion.

A wide variety of eukaryotic hosts are also now available for production of recombinant foreign proteins. As in bacteria, eukaryotic hosts may be transformed with expression systems which produce the desired protein directly, but more commonly signal sequences are provided to effect the secretion of the protein. Eukaryotic systems have the additional advantage that they are able to process introns which may occur in the genomic sequences encoding proteins of higher organisms. Eukaryotic systems also provide a variety of processing mechanisms which result in, for example, glycosylation, carboxy-terminal amidation, oxidation or derivatization of certain amino acid residues, conformational control, and so forth.

Commonly used eukaryotic systems include, but are not limited to, yeast, fungal cells, insect cells, mammalian cells, avian cells, and cells of higher plants. Suitable promoters are available which are compatible and operable for use in each of these host types as are termination sequences and enhancers, e.g. the bacculovirus polyhedron promoter. As above, promoters can be either constitutive or inducible. For example, in mammalian systems, the mouse metallothionene promoter can be induced by the addition of heavy metal ions.

The particulars for the construction of expression systems suitable for desired hosts are known to those in the art. For recombinant production of the protein, the DNA encoding it is suitably ligated into the expression vector of choice and then used to transform the compatible host which is then cultured and maintained under conditions wherein expression of the foreign gene takes place. The protein of the present invention thus produced is recovered from the culture, either by lysing the cells or from the culture medium as appropriate and known to those in the art.

One having ordinary skill in the art can, using well known techniques, isolate the 85 kDa PFK isoform protein produced using such expression systems.

In the protocol using MCPA$_2$ catalytic subunit and PFK isoform that are each separately produced:

The reaction mixture can contain substrate at a final concentration 0.1 nM–500 $\mu$M, preferably 10$\mu$M.

The amount of 40 kDa MCPA$_2$ catalytic subunit used can be 1 pg–1 mg, preferably 20 ng.

The amount of 85 kDa PFK isoform used can be 1 pg–1 mg, preferably 100 ng.

ATP is commercially available from Sigma. The reaction mixture can contain ATP at a final concentration 0.1 $\mu$M–100 $\mu$M.

The reaction mixture can contain test compound at a final concentration 1 pM–100 $\mu$M, preferably 1$\mu$M.

The preferred assay buffer is (final conditions) 100 mM Tris, 4 mM EGTA, 4 mM EDTA, pH 7.0.

The reaction can take place from about 10 seconds to about 30 minutes at about 5° C. to about 37° C. The preferred conditions are 37° C. for 1 minute.

After reaction time has elapsed, the reaction may be terminated by addition of a compound or solution. The preferred method of stopping the reaction is by quenching the reaction solution with butanol.

In preferred embodiments of the invention, the level of phospholipase activity is measured by using a substrate that has a radiolabelled phosphorus which is removed by phospholipase. After the components are maintained for a sufficient time for the reaction to occur, the reaction is stopped and the mixture is passed through a filter which allows free phosphorus to pass through but which does not allow the substrate to pass. The amount of labelled, i.e. unprocessed, substrate is measured using a scintillation counter.

Another aspect of the invention relates to essentially pure 85 kDa PFK isoform. This essentially pure protein may be used as a reagent in the assay for identifying compounds that modulate MCPA$_2$ activity.

Experiments reported in Example 1 have been performed to demonstrate the association between the 85 kDa PFK isoform and the MCPA$_2$ 40 kDa catalytic subunit. The results of these experiments which provide evidence to support this conclusion include:

1) the 50,000-fold copurification of the 85 kDa protein with the 40 kDa catalytic subunit of MCPA$_2$;

2) the comigration during gel filtration chromatography of the 85kDa and 40kDa polypeptides which migrate as a high molecular weight complex (400 kDa) in their native states;

3) the sequence homology of the 85 kDa constituent to PFK;

4) the specific immunoreactivity of the 85 kDa protein constituent with affinity-purified antibodies generated against PFK from rabbit skeletal muscle;

5) the immunoprecipitation of $MCPA_2$ activity utilizing chicken anti-rabbit skeletal muscle PFK IgG;

6) the ability of the 85 kDa polypeptide to act as a specific and reversible affinity adsorbent for myocardial cytosolic phospholipase $A_2$ catalytic activity;

7) the concomitant release of the 85 kDa and 40 kDa polypeptides from ATP agarose during ternary complex affinity chromatography by agents which allosterically modify the conformation of PFK;

8) the attenuation of the thermal denaturation of purified homogeneous myocardial calcium-independent cytosolic phospholipase $A_2$ by PFK;

9) the demonstration that ATP, a known allosteric modulator of PFK, alters the kinetic characteristics and thermal stability of rabbit myocardial cytosolic calcium-independent phospholipase $A_2$;

10) the native molecular weight of the $MCPA_2$ catalytic complex closely corresponds to the known tetrameric quaternary structure of PFK; and, 11) the 11:1 stoichiometry of the 85 kDa constituent to the 40 kDa constituent closely corresponds to a stoichiometric complex comprised of a tetrameric PFK isoform and a 40 kDa $MCPA_2$ catalytic polypeptide.

Collectively, the results of the experiments described in Example 1 provide compelling evidence that a PFK isoform and $MCPA_2$ catalytic subunit are tightly associated and together comprise the phospholipase $A_2$ catalytic complex. These results are entirely consistent with the identification of a phosphofructokinase isoform which serves as the regulatory constituent. These findings provide a rational biochemical explanation for: 1) the selective binding of phospholipase $A_2$ to ATP agarose; 2) the activation of phospholipase $A_2$ catalytic activity by ATP; and 3) the alterations observed in the rate of thermal denaturation of phospholipase $A_2$ activity in the presence of ATP. Since ATP results in allosteric alterations in the conformation and quaternary structures of PFK, and since a phosphofructokinase isoform (which apparently is also sensitive to structural modification by ATP) and phospholipase $A_2$ are tightly associated, the results presented herein provide a logical rationale for the kinetic, chromatographic and physical properties manifest by the myocardial calcium-independent phospholipase $A_2$ catalytic complex.

Myocardial ischemia is accompanied by profound alterations in glycolytic flux which are largely believed to be regulated by allosteric alterations in phosphofructokinase. Indeed, phosphofructokinase occupies a key regulatory position in the modulation of glycolysis, and its importance in cellular metabolism is underscored by the wide variety of metabolites which can modify its activity. Although it is well recognized that many cellular perturbations which effect alterations in glycolytic flux are accompanied by increases in phospholipolysis, the biochemical mechanisms responsible for this coupling have not been elucidated. For example, during early myocardial ischemia an increase in anaerobic glycolysis is accompanied by the selective release of arachidonic acid. Similarly, perturbation of intermediary metabolism in pancreatic islet $\beta$ cells exposed to glucose results in the selective release of arachidonic acid.

The identification of a complex comprised of phospholipase $A_2$ and a phosphofructokinase isoform provides a logical mechanism through which alterations in glycolysis and/or cellular high energy phosphate status can modulate phospholipolysis. Indeed, the multiple interactive metabolic sensory functions inherent in the structure of phosphofructokinase can, through its association with phospholipase $A_2$, be concordantly utilized to regulate alterations in phospholipase $A_2$ activity in response to cellular perturbations. In some tissues, the reasons underlying the coupling of glycolysis to phospholipolysis are evident (e.g., exposure of pancreatic beta cells to glucose resulting in the activation of phospholipase $A_2$, release of arachidonic acid, elevation of intracellular calcium and subsequent insulin secretion) while in others (e.g., accelerated phospholipolysis during myocardial ischemia) the precise biochemical logic underlying this association is not readily apparent. Whatever the case, it seems clear that the association of calcium-independent phospholipase $A_2$ with a phosphofructokinase isoform allows a plethora of complex metabolic relationships to be concordantly assimilated through a known metabolic sensor which results in the regulation of the release of biologically-active fatty acids, the modulation of membrane physical properties and can (at least in the short term) provide a source of fatty acids for mitochondrial beta oxidation. Based upon this reasoning, it seems tenable that the deleterious effects of myocardial ischemia result, in part, from the excessive utilization of an intrinsic regulatory pathway which was designed to respond to alterations in metabolic states but is unable to appropriately respond to the profound and prolonged metabolic demands associated with myocardial ischemia.

A further aspect of the present invention relates to a kit for practicing the above described method of identifying compounds that modulate the activity of myocardial calcium-independent phospholipase $A_2$. One embodiment of such a kit comprises a first container comprising 400 kDa $MCPA_2$ complex, and a second container comprising a labelled substrate such as, for example, 16:0,[$^3$H]18:1 plasmenylcholine. Another embodiment of such a kit comprises a first container comprising 40 kDa $MCPA_2$ catalytic subunit, a second container comprising 85 kDa PFK isoform, and a third container comprising a labelled substrate such as, for example, 16:0,[$^3$H]18:1 plasmenylcholine. Optionally, a fourth container comprising ATP may be provided.

EXAMPLES

Example 1

The following is a description of the experiments performed to demonstrate the association of PFK isoform with $MCPA_2$ catalytic subunit.

Experimental Procedures

Preparation of Synthetic Phospholipids

Synthesis of homogeneous 16:0, [$^3$H]-18:1 plasmenylcholine was performed by dicyclohexylcarbodi-imide-mediated synthesis of [$^3$H]-oleoyl anhydride and subsequent condensation with reverse phase HPLC purified 1-O (Z)-hexadec-1'- enyl-sn-glycero-3-phosphocholine utilizing N,N-dimethyl-4-aminopyridine as catalyst as described in Han, X., et al. (1992) *Anal. Biochem.* 200:119–124, which is incorporated herein by reference.

The resultant radiolabeled glycerophospholipid was purified by sequential TLC and subsequent Partisil SCX-HPLC and the structure and purity of each radiolabeled synthetic product were confirmed by TLC and straight phase HPLC as described in Hazen, S. L., et al. (1990) *J. Biol. Chem.* 265:10622–10630.

Enzyme Assays

Phospholipase $A_2$ activity was assayed by incubating the indicated mass of enzyme with 2 $\mu$M 16:0, [$^3$H]-18:1 plasmenylcholine (introduced by ethanolic injection (10 $\mu$l)) in 100 mM Tris, 4 mM EGTA, pH 7.0 at 37° C. for 1 min (final volume=210 $\mu$l). Reactions were subsequently quenched by addition of 100 $\mu$l of butanol and reaction products in the butanol layer were resolved by TLC prior to quantification by scintillation spectrometry as described in Hazen, S. L., et al. (1990) *J. Biol. Chem.* 265:10622–10630. Reactions were nearly linear with respect to both time and protein concentration under the conditions employed.

Phosphofructokinase in the indicated column fraction or aliquot was assayed at 22° C. at pH 6.5 by a spectrophotometric assay described in Emerk, K., and C. Frieden (1975) *Arch. of Biochem. Biophys.* 168:210–218. Briefly, reactions were initiated by addition of enzyme to tubes containing 50 mM Na[PO$_4$] (pH 6.5 at 22° C.), 1 mM EGTA, 0.2 mM DTT, 5 mM Mg acetate, 25 mM KCl, 0.5 mM NH$_4$Cl, 0.2 mM NADH, 60 $\mu$g/ml lactate dehydrogenase, 120 $\mu$g/ml pyruvate kinase, 0.2 mM phosphoenoyl pyruvate, 0.5 mM fructose-6-phosphate, and 100 $\mu$g/ml fructose-1,6-bisphosphatase. Reaction velocities were quantified by measuring changes in absorbance at 340 nm. The concentration of ATP, when added, was 0.5 mM.

Purification of Myocardial Cytosolic Calcium-Independent Phospholipase $A_2$

Mammalian cytosolic calcium-independent phospholipase $A_2$ was isolated from either rabbit, dog and/or human (transplant recipients suffering from end stage ischemic heart disease) ventricular myocardium by sequential DEAE-Sephacel, chromatofocusing, ATP-agarose and FPLC-Mono Q chromatographies as previously described in Hazen, S. L., et al. (1990) *J. Biol. Chem.* 265:10622–10630 and Hazen, S. L., et al. (1991) Methods in Enzymology, Dennis, et al., Vol.::197, Academic Press, Inc., San Diego, Calif. Gel filtration chromatography of human myocardial cytosolic phospholipase $A_2$ was performed by application of the ATP agarose affinity column eluent (0.3 ml) (specific activity=3 $\mu$mol/mg·min) to tandem columns comprised of Superose 12 (each 1$\times$30 cm) previously equilibrated with 400 mM K[PO$_4$], 25% glycerol, 1 mM M DTT, (pH 7.0). In experiments where both PFK and phospholipase $A_2$ activity were to be determined, fractions from DEAE Sephacel chromatography containing canine myocardial cytosolic phospholipase $A_2$ activity were dialyzed against 20 L of 10 mM imidazole, 10 mM KCl, 25% glycerol, 1 mM DTT, (pH 8.0), loaded onto a previously equilibrated PBE-94 chromatofocusing column. (1.6$\times$30 cm) and eluted at 1.8 ml/min utilizing a buffer comprised of 10% PB96, 5% PB74, 25% glycerol, 1 mM DTT, pH 6.0.

Ternary complex affinity chromatography of partially purified myocardial cytosolic phospholipase $A_2$ was performed utilizing N6-[(6-aminohexyl) -carbamoyl-methyl]-ATP-Sepharose similar to the method of Ramadoss, C. S., et al. (1976) *Arch. Biochem. Biophys.* 175, 487–494, which is incorporated herein by reference, to achieve the single-step purification of PFK. Briefly, column eluents containing canine myocardial cytosolic phospholipase $A_2$ activity purified by sequential DEAE-Sephacel and chromatofocusing columns as described Hazen, S. L., et al. (1990) *J. Biol. Chem.* 265:10622–10630; specific activity=0.5 $\mu$mol/mg·min) were applied to a 1$\times$1-cm ATP agarose affinity column previously equilibrated with 10 mM imidazole, 25% glycerol, 1 mMDTT (pH 8.3). Following extensive washing with equilibration buffer, the bound proteins of interest were eluted by sequential application of the following ligands in equilibration buffer: 50 $\mu$M fructose-6-phosphate, buffer wash, 50 $\mu$M ADP, buffer wash, and finally 50 $\mu$M fructose-6-phosphate plus 50 $\mu$M ADP in the volumes indicated in the figure legends.

Preparation of Affinity-Purified Antibodies to Rabbit Phosphofructokinase

White leg horn laying hens received an initial injection into the pectoral muscle of 100–200 $\mu$g skeletal muscle phosphofructokinase (from rabbit) dissolved in 0.5 ml of 125 mM Tris buffer (pH 8.0) emulsified with an equal volume of complete Freund's adjuvant. One week later, hens received a second injection of 100–200 $\mu$g of rabbit phosphofructokinase (emulsified in incomplete adjuvant). Similar monthly booster injections followed. Hen eggs were collected daily, labeled and stored for no more than three weeks at 4° C. prior to processing. Crude polyclonal IgG was isolated from egg yolks by differential precipitation with dextran sulfate and Na$_2$SO$_4$ employing the method of Jensenius, J. C., et al. (1981) *J. Immunol. Methods* 46:63–68.

Chicken anti-rabbit skeletal muscle PFK IgG was subsequently affinity purified from this mixture utilizing immobilized rabbit skeletal muscle PFK. Briefly, the affinity resin was initially washed with 0.1M glycine (pH 2.5) and was subsequently equilibrated with 50 mM Tris, 150 mMNaCl (pH 8.1) at a flow rate of 1 ml/min. Next, crude polyclonal chicken anti-rabbit skeletal muscle PFK IgG was dissolved in 50 mM Tris, 150 mM NaCl (pH 8.1) at a concentration of 2 mg/ml and applied to a 1$\times$1 cm column of rabbit skeletal muscle PFK-agarose (Sigma Chemical Company). The column with bound antibody was extensively washed with 50 mM Tris buffer containing 150 mM NaCl (pH 8.1) and recovery of affinity purified antibody was effected by application of either 4M MgCl$_2$ or 0.1M glycine buffer (pH 2.5). Affinity-purified chicken anti-rabbit skeletal muscle PFK IgG was immediately dialyzed into the buffer of choice prior to use.

Immunoprecipitation and TCA Precipitation

Immobilization of either the 85 kDa phospholipase $A_2$ binding protein or the affinity-purified chicken anti-rabbit skeletal muscle phosphofructokinase IgG was performed utilizing CNBr-activated Sepharose 4B (Pharmacia LKB Biotechnology) according to the manufacturer's instructions. Immunoprecipitations were performed by transferring a small aliquot of antibody immobilized to Sepharose 4B beads (500 $\mu$l) to a 10$\times$75 mm disposable borosilicate test tube. Next, tubes were spun at 2000$\times$ g for 5 min and the supernatant was removed. Aliquots of the indicated samples (approx. 200–300 $\mu$l) were added to the beads, agitated gently for 5 min at 4° C. and subsequently spun at 2000$\times$ g for 5 min at 4° C. Nonspecific binding was minimized by addition of either 0.5M NaCl during immunoprecipitations where either PFK or phospholipase $A_2$ activity were to be measured or by addition of 150 mM NaCl, 50 mM Tris, 0.05% Tween 20 (pH 8.1) where the presence of detergents was not contraindicated. After centrifugation at 2000× g for 5 min the supernatants were gently removed and analyzed by assay of phospholipase $A_2$ activity and by SDS-PAGE. To recover proteins bound to the immunoaffinity resin, pellets were washed several times with buffer and antigen bound to immobilized immunoglobulin was recovered by application of 50 mM Tris, 4M $MgCl_2$ (pH 8.1), subsequent centrifugation and dialysis of the resultant supernatant.

Iodination of Polypeptides, Sodium Dodecylsulfate-Polyacrylamide Gel Electrophoresis, Western Blotting and Autoradiography Proteins in the indicated fractions (=100 µl) were iodinated utilizing 250 µCi of [$^{125}$I] Bolton-Hunter reagent (specific activity=4400 Ci/mol). Sodium dodecyl sulfate-polyacrylamide gel electrophoresis (either 10% or 10–15% gradient gels as indicated) was subsequently performed, the gels were fixed, dried and, finally, exposed to Kodak XR-5 film. Western blotting was performed utilizing 10% sodium dodecylsulfate polyacrylamide gels by first transferring protein replicas to nitrocellulose paper utilizing a Hoeffer blotting apparatus. Electroblots were blocked by conventional methods with buffer (150 mM NaCl, 50 mM Tris, 0.05% Tween 20, 0.1% $NaN_3$, pH 8.1) (TBST) containing 20% fetal calf serum. Subsequently, blots were incubated with affinity-purified chicken anti-rabbit skeletal muscle phosphofructokinase antibody (1 mg/ml) containing 20% fetal calf serum in TBST buffer for 1 h at room temperature with gentle rocking. Exhaustive washing with TBST buffer followed. Immunoreactive proteins were identified by autoradiography following incubation with rabbit anti-chicken PFK IgG and [$^{125}$I] protein A employing conventional methods.

Miscellaneous Procedures and Sources of Materials

Either BioRad or QuantiGold (Diversified Biotech) protein assay kits were utilized for measurement of protein content according to instructions supplied by the manufacturer. Native polyacrylamide gel electrophoresis was performed in the absence of SDS utilizing a discontinuous nondenaturing 10% gel with the stacking gel, resolving gel and reservoir buffers at pH 6.8, 8.8-and 8.3, respectively, and reducing gels were run with the addition of 100 mM dithiothreitol to both the sample buffer and the gel/reservoir buffers as described in Blackshear, P. J. (1984) Methods in Enzymology, Vol.:104 Academic Press, Inc., San Diego, Calif., which is incorporated herein by reference. [$^{125}$I] Bolton Hunter reagent and [$^{125}$I] Protein A were purchased from Amersham. All other radiolabeled starting materials were purchased from DuPont New England Nuclear. Bovine heart choline and ethanolamine glycerophospholipids were purchased from Avanti Polar Lipids while free fatty acids were obtained from Nu Chek Prep Inc. Fructose phosphates, nucleotides, ATP-agarose, skeletal muscle PFK from rabbit, PFK-agarose, lactate dehydrogenase, pyruvate kinase, fructose 1,6 bisphosphatase, phosphoenol-pyruvate and most buffer reagents were obtained from Sigma Chemical Co. Rabbit anti-chicken serum was obtained from Organon Teknika Corp. DEAE-Sephacel PBE-94, PB74, PB96, Mono Q and Superose 12 columns were purchased from Pharmacia LKB Biotechnology, Inc. All HPLC columns were purchased from PJ Cobert. Detergents and molecular weight standards were purchased from Pierce Chemical Company. Dicyclohexylcarbodiimide and N,N-dimethyl-4-aminopyridine were obtained from Aldrich. Most other reagents were obtained from either Sigma Chemical Company or Fisher Scientific Co.

Results

The 40 kDa Polypeptide Catalyzing Myocardial Cytosolic Calcium-Independent Phospholipase As Activity is Associated with an 85 kDa Polypeptide Application of highly purified human myocardial cytosolic calcium-independent phospholipase $A_2$ (ATP-agarose eluent; specific activity=3 µmol/mg·min) to tandem columns comprised of Superose 12 demonstrated that cytosolic phospholipase $A_2$ activity migrated as a high molecular weight complex exhibiting an apparent molecular weight of 400 kDa even in the presence of supraphysiologic ionic strength column buffers (e.g., 400 mM $K[PO_4]$) (FIG. 1). Similar results have also been obtained with both canine and rabbit myocardial cytosolic phospholipases $A_2$. Since the polypeptide catalyzing myocardial cytosolic calcium-independent phospholipase $A_2$ activity is a 40 kDa protein in all mammalian species thus far examined (i.e., canine (Hazen, S. L., et al. (1990) J. Biol. Chem. 265:10622–10630), rabbit (Hazen, S. L., R. W. Gross, (1991) J. Biol. Chem. 266:14526–14534), and human (Hazen, S. L., and R. W. Gross, (1991) Biochem. J. 280:581–587)), the protein constituents which comigrated with calcium-independent phospholipase $A_2$ catalytic activity during gel filtration chromatography were iodinated, resolved by SDS-PAGE and visualized by autoradiography. Only the 40 kDa catalytic polypeptide and an 85 kDa polypeptide were present in the fractions containing the majority of $PLA_2$ activity.

FIG. 1 illustrates the results of gel filtration chromatography of human myocardial cytosolic calcium-independent phospholipase $A_2$ activity.

In FIG. 1, panel A, a 300 µl aliquot of human myocardial cytosolic calcium-independent phospholipase $A_2$ (ATP-agarose eluent; specific activity =3 µmol/mg·min) was applied to tandem Superose 12 columns previously equilibrated with 400 mM $K[PO_4]$, 25% glycerol, pH 7.0 at 4° C. Phospholipase $A_2$ activity in column eluents was assayed by incubation of aliquots of column fractions with 1-O-(Z)-hexadec-1-enyl-2-[9'10'$^3$H]-octade-9'-enoyl-sn-glycero-3-phosphocholine, separation of released radiolabeled oleic acid (•) by TLC and quantification by scintillation spectrometry as described in "Experimental Procedures". Insert:plot of $K_{AV}$ vs. $M_r$ utilizing ovalbumin, albumin, aldolase, catalase and ferritin standards.

In FIG. 1, panel B, aliquots from tandem Superose 12 gel filtration chromatography corresponding to the peak of phospholipase $A_2$ activity were iodinated with Bolton Hunter reagent and electrophoresed on 10% sodium dodecyl sulfate polyacrylamide gels prior to fixation, drying and visualization by autoradiography as described in "Experimental Procedures". The intensity of the 40 kDa band relative to the 85 kDa band (as determined by scanning densitometry) remained constant throughout the elution of the phospholipase $A_2$ activity peak and the elution of both protein constituents precisely paralleled the elution profile of phospholipase $A_2$ activity during gel filtration chromatography. The ratio of the integrated areas of the 85 and 40 kDa bands was 11:1 as assessed by scanning densitometry. In both reducing and non-reducing denaturing polyacrylamide gels, the fraction possessing the peak phospholipase $A_2$ activity demonstrated a single intense band in which both the 40 kDa and 85 kDa constituents comigrated.

Figure 2:
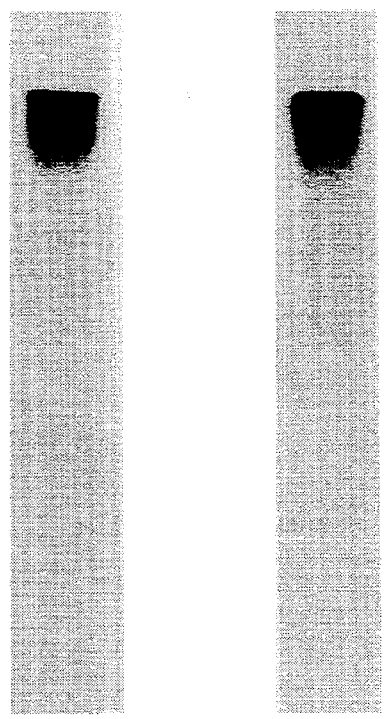
FIG. 2 shows the results of denaturing polyacrylamide gel electrophoresis of human myocardial cytosolic gel filtration eluent.

FIG. 2 shows the results of denaturing polyacrylamide gel electrophoresis of human myocardial cytosolic gel filtration eluent. An aliquot of the peak fraction (fraction 88) from tandem Superose 12 chromatography of human myocardial cytosolic phospholipase $A_2$ activity (FIG. 1) was iodinated with [$^{125}$I] Bolton Hunter reagent and subsequently analyzed by denaturing polyacrylamide gel electrophoresis under both reducing and non-reducing conditions as described in "Experimental Procedures". The gels were subsequently fixed, dried and individual proteins were visualized by autoradiography as described in "Experimental Procedures".

Although the 85 kDa polypeptide co-purifies over 50,000-fold with myocardial cytosolic calcium-independent phospholipase $A_2$, and the 85 kDa polypeptide was the only protein constituent (other than the 40 kDa catalytic polypeptide) identified in gel filtration eluents of highly purified phospholipase $A_2$, additional experiments were performed to substantiate the direct interaction between the 40 kDa polypeptide (catalytic polypeptide) and the 85 kDa putative regulatory constituent.

Figure 3:
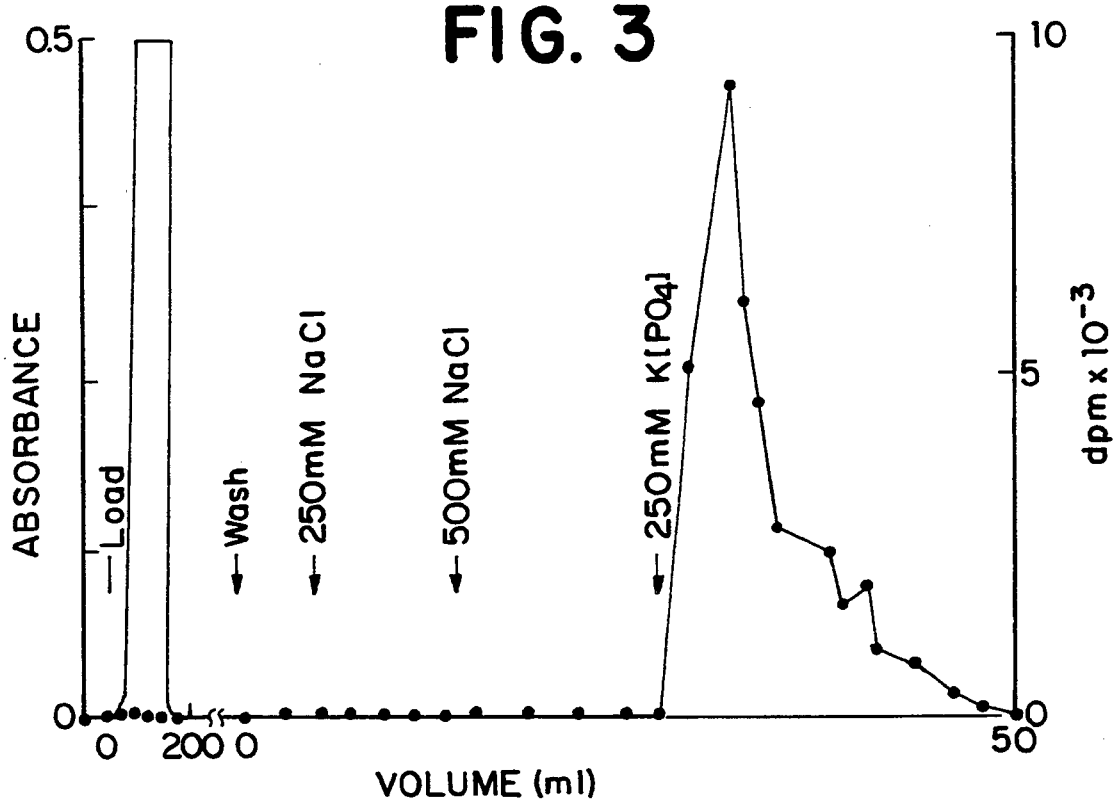
FIG. 3 shows the quantitative absorbance of affinity purified phospholipase $A_2$ activity when partially purified canine myocardial cytosolic phospholipase $A_2$ (chromatofocusing column eluent) was applied to an affinity matrix to which the 85 kDa protein constituent was covalently bound.

It has been previously demonstrated that application of ATP-agarose affinity purified myocardial cytosolic phospholipase $A_2$ to a Mono Q FPLC column results in the resolution of the 40 kDa catalytic polypeptide from other proteins present in that preparation (Hazen, S. L., Stuppy, R. J., and Gross, R. W. (1990) J. Biol. Chem. 265:10622-10630). Mono Q fractions containing the near-homogeneous 85 kDa polypeptide were first identified by SDS-PAGE after silver staining and were subsequently utilized to prepare an affinity matrix to which the 85 kDa protein constituent was covalently bound. When partially purified canine myocardial cytosolic phospholipase $A_2$ (chromatofocusing column eluent) was applied to this matrix, phospholipase $A_2$ activity was quantitatively adsorbed (FIG. 3). Subsequent application of high ionic strength buffer (either 250 mM NaCl or 500 mM NaCl) failed to elute phospholipase $A_2$ enzymatic activity. However, application of inorganic phosphate (250 mM K[PO$_4$]) resulted in the near-quantitative recovery of applied phospholipase $A_2$ activity (FIG. 3). Thus, the 85 kDa affinity matrix was highly selective for the binding of phospholipase $A_2$ activity since the overwhelming majority (>95%) of protein loaded onto the affinity matrix eluted in the void volume while all of the phospholipase $A_2$ catalytic activity was specifically bound under the conditions employed.

FIG. 3 shows the results of affinity chromatography with 85 kDa agarose. Myocardial cytosolic phospholipase $A_2$ (purified by sequential DEAE-Sephacel and chromatofocusing chromatographies) was applied to an 85 kDa affinity matrix prepared as described in "Experimental Procedures". After loading, the column was subsequently washed with the indicated volumes of buffer, buffer containing 250 mM NaCl, buffer containing 500 mM NaCl and buffer containing 250 mM K[PO$_4$]. Phospholipase $A_2$ activity in column eluents was assessed as described in "Experimental Procedures". (•) depicts fatty acid released; (—) uv absorbance at 280 nm.

Figure 4:
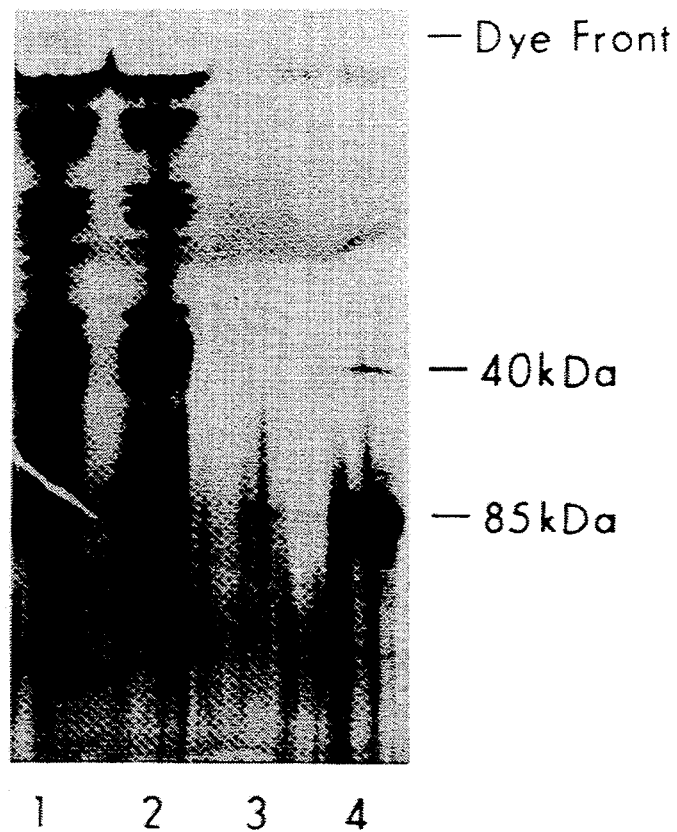
FIG. 4 illustrates the results of sodium dodecylsulfate-polyacrylamide gel electrophoresis and subsequent silver staining of the fraction containing the peak of phospholipase $A_2$ activity.

Evaluation of the fraction containing the peak of phospholipase $A_2$ activity by sodium dodecylsulfate polyacrylamide gel electrophoresis and subsequent silver staining demonstrated the presence of both the 85 kDa and 40 kDa constituents (FIG. 4). Thus, the 85 kDa affinity matrix has specific affinity for both 85 kDa protein constituents and the 40 kDa catalytic polypeptide.

FIG. 4 shows the results of SDS-PAGE of the 85 kDa agarose column. Aliquots of column fractions from the 85 kDa affinity chromatography (FIG. 3) including the load (lane 1), void (lane 2), 500 mM NaCl (lane 3) and 250 mM K[PO$_4$] (lane 4) were boiled in 10% SDS sample buffer and applied to a 10-15% gradient SDS-PAGE gel, electrophoresed and visualized by silver staining as described in "Experimental Procedures".

The 85 kDa Protein is Highly Homologous to Phosphofructokinase

Attempts at N-terminal sequence analysis of the canine myocardial 85 kDa protein constituent were unsuccessful suggesting that it is N-blocked. Accordingly, fractions containing near-homogeneous 85 kDa polypeptide were first applied to a 10% sodium dodecylsulfate polyacrylamide gel, blotted onto PVDF paper, cleaved in situ utilizing trypsin, and released peptides were purified utilizing sequential C$_4$ reverse phase and C$_8$ reverse phase chromatography. Two well-resolved peptides were sequenced by automated Edman degradation yielding the sequences listed in Table 1. Data base searches demonstrated significant homologies (16 out of 18 identities between SEQ ID NO:1 and SEQ ID NO:2 (PFK) and 13 out of 16 identities between SEQ ID NO:3 and SEQ ID NO:4 (PFK). These similarities demonstrate sequence homology between the 85 kDa canine isoform and rabbit skeletal muscle phosphofructokinase.

TABLE I

| Homology between the 85kda canine myocardial constituent which copurifies with Calcium-independent PLA$_2$ and rabbit PFK | |
|---|---|
| SEQ ID NO: 1 | Ile Ala Val Leu Thr Gln Gln Gly Asp Ala Gln Gly Met Asn Ala Ala Val Arg |
| SEQ ID NO: 2 | Ile Ala Val Leu Thr Ser Gly Gly Asp Ala Gln Gly Met Asn Ala Ala Val Arg |
| SEQ ID NO: 3 | Val Leu Gly His Met Ser Gly Gly Cys Ser Pro Thr Pro Phe Asp Arg |
| SEQ ID NO: 4 | Val Leu Gly His Met Gln Gln Gly Gly Ser Pro Thr Pro Phe Asp Arg |

Fractions containing near homogeneous 85 kDa polypeptide were run on 10% sodium dodecyl sulfate polyacrylamide gels blotted onto PVDF paper, cleaved utilizing trypsin, and released peptides were purified utilizing sequential C$_4$ reverse phase and C$_8$ reverse phase chromatographies. Two well resolved peptides (SEQ ID NO:1 and SEQ ID NO:3) were sequenced by automated Edman degradation resulting in the sequences listed above. SEQ ID NO:1 and SEQ ID NO:3 are sequences obtained from the 85 kDa constituent which copurifies with phospholipase $A_2$ while SEQ ID NO:2 and SEQ ID NO:4 are sequences of rabbit skeletal muscle phosphofructokinase.

Figure 5:
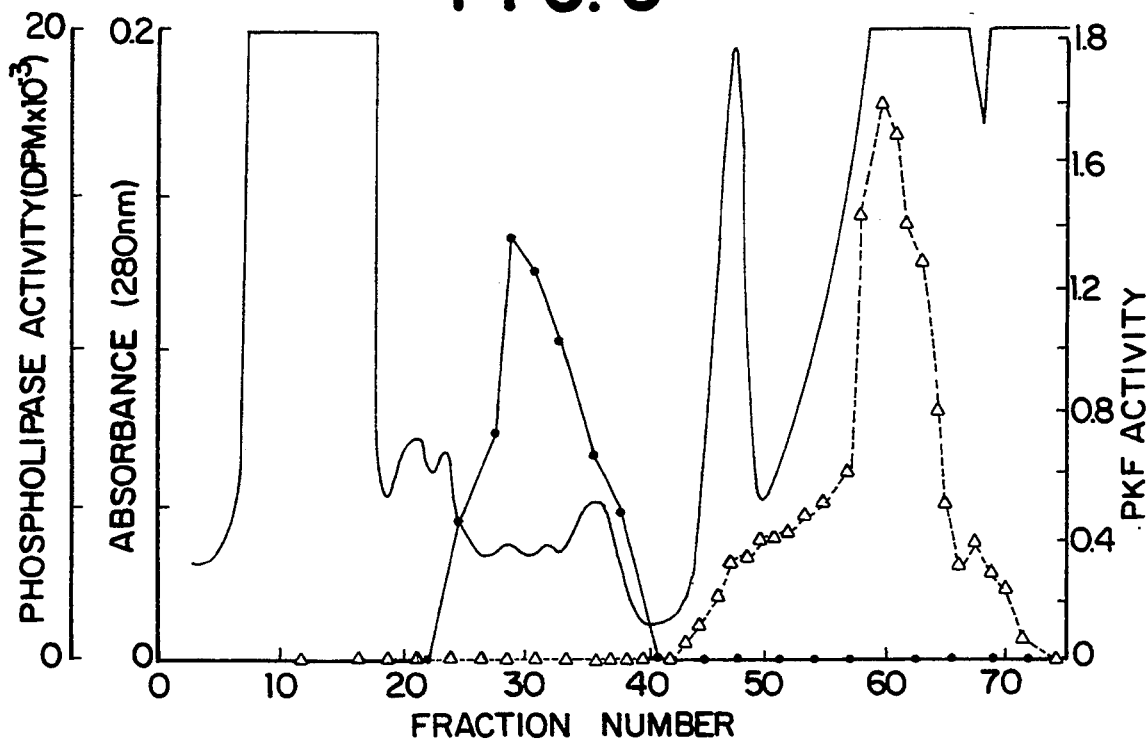
FIG. 5 depicts the chromatofocusing profile of rabbit myocardial cytosolic phospholipase $A_2$ activity and phosphofructokinase activity.

Comparison Between the Chromatographic Profiles of Phosphofructokinase Mass and Activity During the Purification of Myocardial Cytosolic Calcium-Independent Phospholipase $A_2$ Despite the primary sequence homology between the 85 kDa constituent and phosphofructokinase, no intrinsic phosphofructokinase activity could be demonstrated in chromatofocusing eluents containing phospholipase $A_2$ activity after the chromatofocusing column step. Indeed, examination of the elution profiles of phospholipase $A_2$ activity and PFK activities during chromatofocusing chromatography demonstrated the complete resolution of phospholipase $A_2$ and PFK catalytic activity. FIG. 5 depicts the chromatofocusing profile of rabbit myocardial cytosolic phospholipase $A_2$ activity and phosphofructokinase activity. The DEAE-Sephacel eluent from rabbit myocardial cytosol was applied to a chromatofocusing column as described in "Experimental Procedures". After loading, the column was developed by generation of an in situ pH gradient as described in "Experimental Procedures". Calcium-independent phospholipase $A_2$ activity (•) and phosphofructokinase activity (▲) in column fractions were determined as described in "Experimental Procedures"; (−) uv absorbance at 280 nm.

To determine if the 85 kDa constituent homologous to PFK was immunologically related to phosphofructokinase and if phosphofructokinase immunoreactive material co-chromatographed with phospholipase $A_2$ activity, Western analyses were performed. Polyclonal antibodies to rabbit skeletal muscle phosphofructokinase from rabbit were generated in hyperimmunized chickens and subsequently affinity purified utilizing a PFK-agarose affinity matrix as described in "Experimental Procedures".

Figure 6:
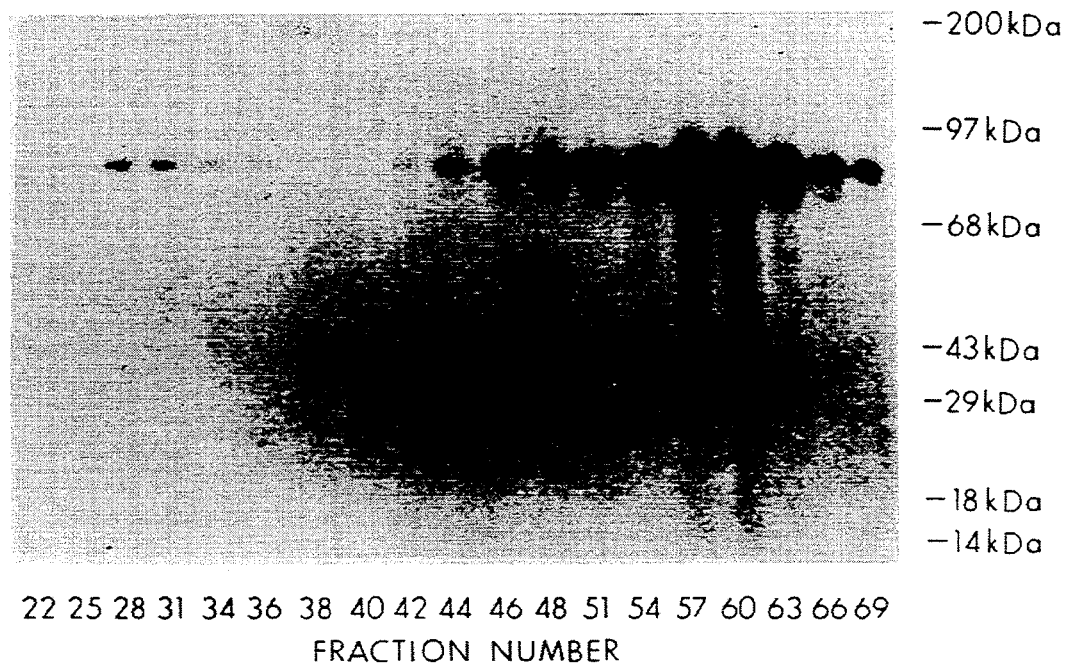
FIG. 6 depicts the specificity of affinity purified chicken anti-rabbit skeletal muscle PFK IgG.

FIG. 6 depicts the specificity of affinitypurified chicken anti-rabbit skeletal muscle PFK IgG. The specificity of affinity-purified chicken anti-rabbit skeletal muscle IgG was assessed by Western analysis of crude myocardial cytosol as described in "Experimental Procedures". The molecular mass of the single immunoreactive species was determined from the profiles of standards run on an adjacent lane and is indicated on the right. The specificity of the immunopurified polyclonal chicken anti-rabbit skeletal muscle phosphofructokinase IgG is underscored by the fact that Western blots of the cytosol contained only a single intense immunoreactive protein at 85 kDa corresponding to the known molecular weight of phosphofructokinase.

Western blot analyses of eluents from chromatofocusing chromatography utilizing this affinity-purified polyclonal chicken anti-rabbit skeletal muscle PFK IgG demonstrated the presence of a major (fractions 44–69) and a minor (fractions 28–34) peak of immunoreactive material. Proteins possessing antigenic determinants recognized by affinity purified chicken anti-rabbit skeletal muscle phosphofructokinase IgG were visualized utilizing [$^{125}$I] Protein A as described in "Experimental Procedures". Numbers below lanes represent the fraction numbers of eluents from the chromatofocusing column depicted in FIG. 5. The mobility of molecular weight standards run on adjacent lanes is indicated on the right.

As expected, chromatofocusing column eluents which possessed phosphofructokinase catalytic activity (fractions 24–38) also contained the overwhelming majority (>99%) of 85 kDa immunoreactive mass (FIG. 6). Remarkably, elution of the minor peak of immunoreactive 85 kDa protein precisely paralleled the elution of calcium-independent phospholipase $A_2$ activity with a distinct nadir prior to the elution of the bulk of immunoreactive PFK mass and PFK catalytic activity. Thus, although the 85 kDa protein which copurifies with calcium-independent phospholipase $A_2$ does not possess demonstrable PFK catalytic activity, it has sequence homology to, shares antigenic determinants with, and possesses physical properties similar to skeletal muscle PFK from rabbit.

Figure 7A:
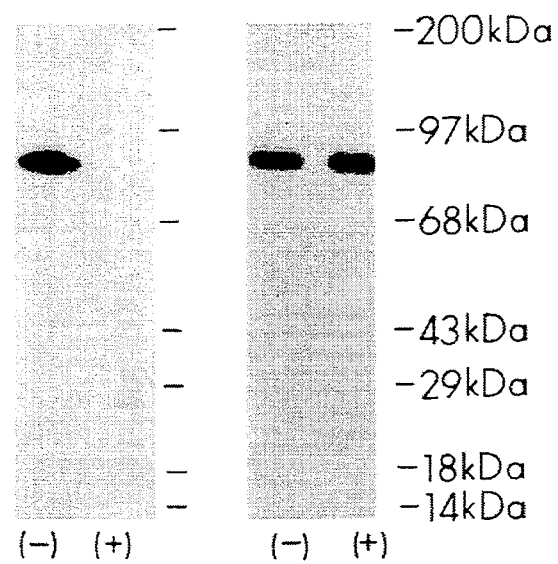
FIG. 7 shows the results of immunoprecipitation of canine myocardial cytosolic phospholipase $A_2$ activity utilizing immobilized anti-PFK IgG.
Figure 7B:
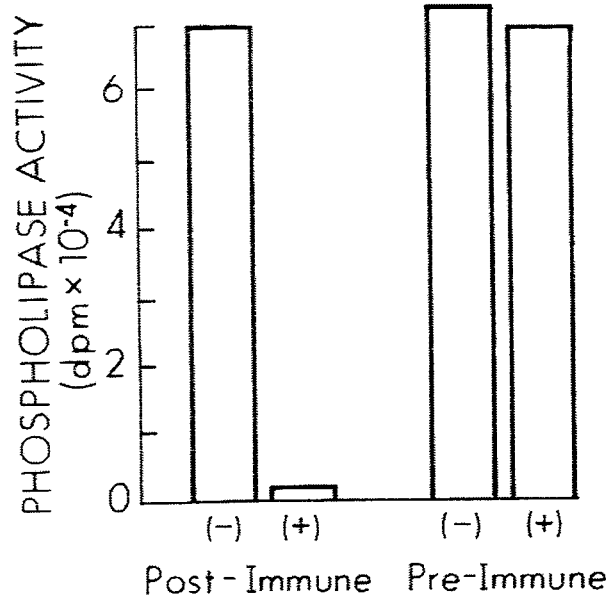

Immunoprecipitation of Myocardial Cytosolic Phospholipase $A_2$ Activity Utilizing Immobilized Anti-PFK IgG To further demonstrate a direct interaction between the 85 kDa PFK isoform and myocardial cytosolic calcium-independent phospholipase $A_2$, immunoprecipitation experiments were performed utilizing immobilized affinity-purified polyclonal antibodies to skeletal muscle PFK from rabbit. Chromatofocusing eluents containing the majority of phospholipase $A_2$ activity were incubated with either immobilized chicken anti-rabbit PFK IgG or immobilized preimmune IgG as described in "Experimental Procedures". Analysis of phospholipase $A_2$ activity in the supernatants after treatment with antibody-coated beads and subsequent centrifugation demonstrated that incubation of phospholipase $A_2$ with chicken anti-rabbit PFK IgG-coated beads removed greater than 95% of phospholipase $A_2$ catalytic activity while incubation with preimmune immunoglobulin-coated beads failed to remove phospholipase $A_2$ catalytic activity. FIG. 7 shows the results of immunoprecipitation of canine myocardial cytosolic phospholipase $A_2$ activity utilizing immobilized anti-PFK IgG. An aliquot of the peak fraction of phospholipase $A_2$ activity from chromatofocusing chromatography was incubated with either immobilized chicken anti-rabbit skeletal muscle PFK IgG (Left) or chicken preimmune IgG coated beads (Right) as described in "Experimental Procedures". Complete immunoprecipitation of 85 kDa mass utilizing affinity-purified chicken anti-rabbit skeletal muscle PFK IgG was confirmed by Western analysis (top left) and the absence of immunoprecipitation of 85 kDa mass utilizing preimmune IgG coated beads was also confirmed (top right). Phospholipase $A_2$ activity remaining in the supernatant was determined utilizing 1-0-(Z)-hexadec-1'-enyl-2-[9'10'$^3$H]-octadec-9'-enoyl-sn-glycero-3-phosphocholine substrate as described in "Experimental Procedures". Complete immunoprecipitation of 85 kDa mass utilizing affinity purified chicken anti-rabbit skeletal muscle IgG was confirmed by Western analysis (top left) and the absence of immunoprecipitation of 85 kDa mass utilizing preimmune IgG coated beads was also confirmed (top right) . Phospholipase $A_2$ activity was completely immunoprecipitated by utilizing chicken anti-rabbit phosphofructokinase coated protein A Sepharose beads (bottom left) and was not affected through utilization of preimmune IgG coated beads (bottom right). Western blot analysis of these fractions confirmed the near-quantitative removal of the 85 kDa polypeptide utilizing immobilized anti-PFK IgG and the absence of significant removal of the 85 kDa putative regulatory constituent utilizing immobilized preimmune immunoglobulin.

Figure 8:
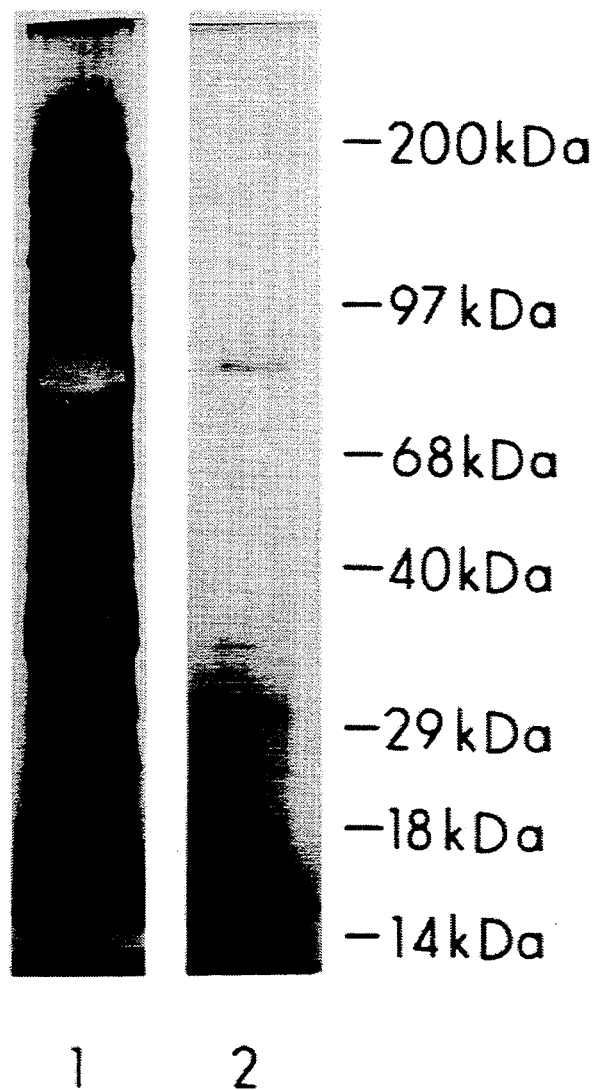
FIG. 8 shows the results of SDS-PAGE of proteins immunoprecipitated by immobilized chicken anti-rabbit phosphofructokinase IgG or immobilized preimmune IgG.

Recovery of immunoprecipitated proteins by boiling the washed beads in 10% SDS sample buffer as described in "Experimental Procedures" and performing subsequent sodium dodecylsulfate-polyacrylamide gel electrophoresis and silver staining demonstrated that the major immunoprecipitated protein is an 85 kDa polypeptide corresponding to the known molecular weight of myocardial PFK. FIG. 8 shows the results of SDS-PAGE of proteins immunoprecipitated by immobilized chicken anti-rabbit phosphofructokinase IgG or immobilized preimmune IgG. Lane 1 is an aliquot of the chromatofocusing fraction containing the peak of phospholipase $A_2$ activity (fraction #60 in FIG. 5) which was applied to 10–15% SDS-PAGE gradient gel, electrophoresed and subsequently visualized by silver staining. Lane 2 contains proteins which were specifically immunoprecipitated utilizing chicken anti-rabbit skeletal muscle PFK polyclonal IgG and were recovered from the precipitated beads by boiling in 10% SDS as described in "Experimental Procedures". Recovered proteins were subsequently electrophoresed on a 10–15% gradient SDS-PAGE gel and visualized after silver staining.

Ternary Complex Affinity Chromatography

Figure 9:
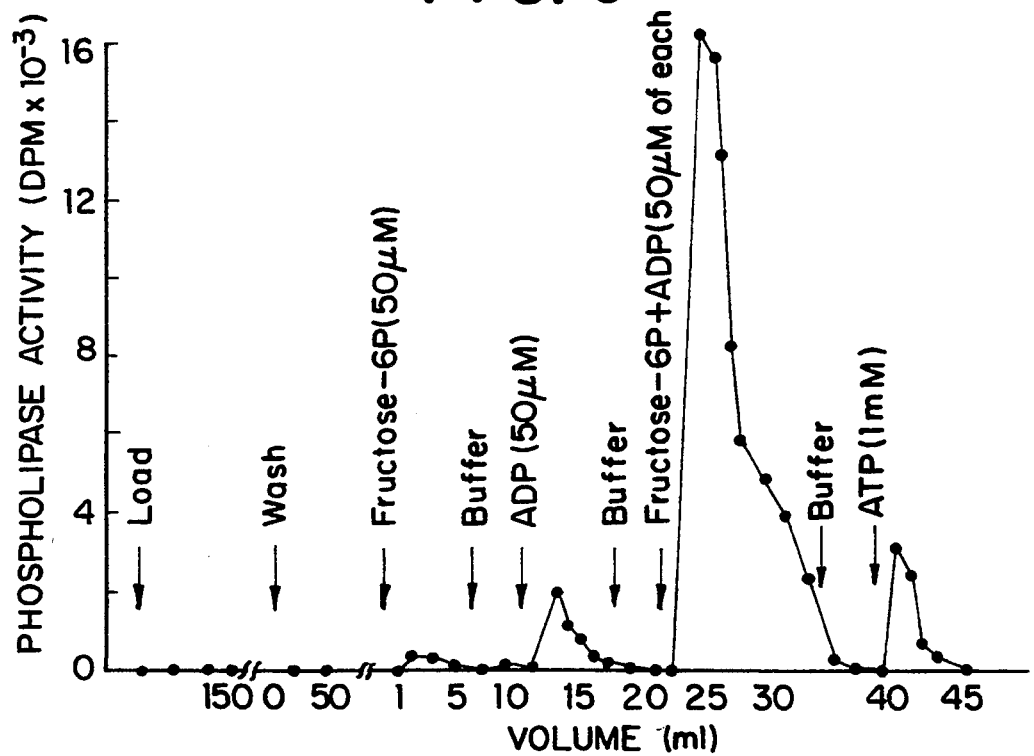
FIG. 9 shows the results of ATP agarose matrix ternary complex chromatography.

To further substantiate the interaction of the 85 kDa PFK isoform with myocardial cytosolic phospholipase $A_2$, an additional independent method was employed. Phosphofructokinase from different sources can be prepared in a near-homogeneous form by ternary complex affinity chromatography employing two ligands which together can allosterically modify the conformation of phosphofructokinase. Accordingly, the chromatofocusing eluent containing phospholipase $A_2$ activity was applied to an ATP agarose matrix as described in "Experimental Procedures" which, as has been previously demonstrated, specifically and quantitatively binds phospholipase $A_2$ catalytic activity. FIG. 9 shows the results of ATP agarose matrix ternary complex chromatography. The fractions containing phospholipase $A_2$ enzymic activity after chromatofocusing chromatography were applied to an ATP agarose affinity column and the column was washed with buffer alone, buffer containing 50 $\mu$M fructose 6-P, buffer alone and containing 50 $\mu$M ADP in the indicated volumes. Phospholipase $A_2$ activity was eluted by application of buffer containing both 50 $\mu$M ADP and 50 $\mu$M fructose 6-P as described in "Experimental Procedures". Aliquots of column fractions were assayed for phospholipase $A_2$ activity utilizing 1-0-(2)-hexadecyl'-enyl-2-0-[9,10$^3$H]octadec-9'-enoyl-sn-glycero-3-phosphocholine substrate as described in "Experimental Procedures". (•) fatty acid release. Although neither fructose-6-phosphate (50 $\mu$M) nor ADP alone (50 $\mu$M) resulted in the elution of substantial calcium-independent phospholipase $A_2$ activity, application of both fructose-6-phosphate and ADP together (50 $\mu$M of each) resulted in the near-quantitative recovery or phospholipase $A_2$ catalytic activity. This single step resulted in the 42-fold purification of myocardial cytosolic phospholipase $A_2$ activity in 78% overall yield. Thus, ATP-agarose ternary complex chromatography utilizing PFK allosteric modifiers resulted in the concomitant, highly specific and reversible adsorption of both the PFK isoform and myocardial cytosolic calcium-independent phospholipase $A_2$, further corroborating the interaction between these two proteins.

Figure 10:
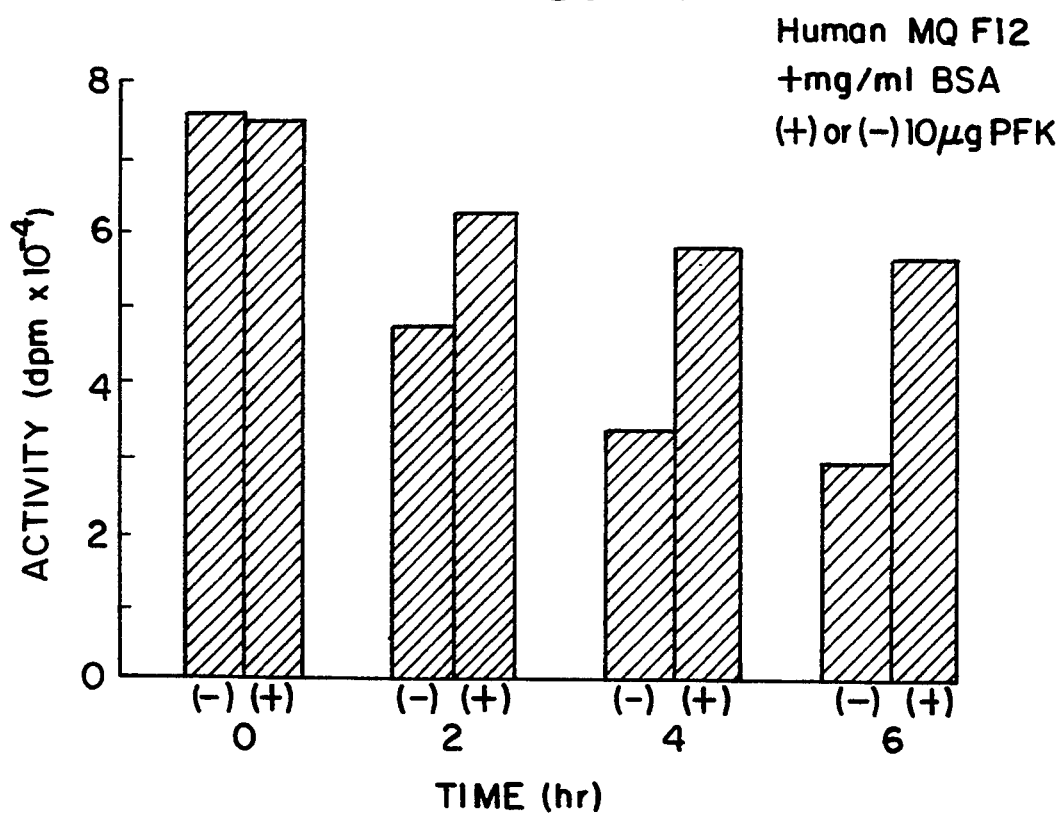
FIG. 10 illustrates that phosphofructokinase attenuates the thermal denaturation of purified human myocardial cytosolic phospholipase $A_2$.

Phosphofructokinase Attenuation of the Thermal Denaturation of Purified Human Myocardial Cytosolic Phospholipase $A_2$ Activity Resolution of the myocardial cytosolic phospholipase $A_2$ catalytic polypeptide (40 kDa) from the 85 kDa PFK isoform during Mono Q chromatography results in a dramatic increase in the thermal lability of the catalytic polypeptide. To further assess the specificity of the interaction between phospholipase $A_2$ and the 85 kDa phosphofructokinase isoform, experiments were performed in which near-homogeneous myocardial cytosolic phospholipase $A_2$ was incubated in the presence or absence of 10 $\mu$g of skeletal muscle PFK from rabbit and excess bovine serum albumin (to minimize the effects of both non-specific binding and adsorption in dilute samples). Addition of skeletal muscle PFK (from rabbit) substantially attenuated the thermal denaturation of near-homogeneous myocardial cytosolic phospholipase $A_2$. FIG. 10 illustrates that phosphofructokinase attenuates the denaturation of purified human myocardial cytosolic phospholipase $A_2$. Highly purified human myocardial cytosolic phospholipase $A_2$ (Mono Q eluent; specific activity = 10 $\mu$mol/mg min) was incubated at 4° C. with excess bovine serum albumin (1 mg/ml) in the presence (+) or absence (−) of 10 $\mu$g of rabbit skeletal muscle phosphofructokinase. Remaining phospholipase $A_2$ activity was subsequently determined by assay of aliquots removed at the indicated times as described in "Experimental Procedures"; (•), fatty acid release.

Example 2

The ability of a test compound to modulate MCPA$_2$ activity is investigated using a reaction assay that employs an MCPA$_2$ complex purified from tissue.

The basic reaction mixture contains:
1 $\mu$g 400 kDa MCPA$_2$ complex;
10 $\mu$M 16:0, [$^3$H] 18:1 plasmenylcholine;
reaction buffer having, at final concentration, 100 mM Tris, 4 mM EGTA, 4 mM EDTA, pH 7.0; and 10 $\mu$M ATP.

Six reaction assays (five test assays, one control) are performed using stepwise dilutions of test compound. The control assay has no test compound and consists of reaction buffer at final concentration (100 mM Tris, 4 mM EGTA, 4 mM EDTA, pH 7.0). The test assays include 0.01 $\mu$M test compound, 0.1 $\mu$M test compound, 1 $\mu$M test compound, 10 $\mu$M test compound and 100 $\mu$M test compound, respectively.

The reactions proceed at 37° C. for 1 minute. After reaction time has elapsed, the reaction may be terminated by addition of 100 $\mu$l of butanol. Reaction products in the butanol layer are resolved by TLC prior to quantification by scintillation spectrometry.

Example 3

The ability of a test compound to modulate MCPA$_2$ activity is investigated using a test assay that employs MCPA$_2$ catalytic subunit and PFK isoform that are produced separately.

The basic reaction mixture contains:
20 ng 40 kDa MCPA$_2$ catalytic subunit;
100 ng 85 kDa PFK isoform;
10 $\mu$M 16:0, [$^3$H] 18:1 plasmenylcholine;
reaction buffer having, at final concentration, 100 mM Tris, 4 mM EGTA, 4 mM EDTA, pH 7.0; and 10 $\mu$M ATP.

Six reaction assays (five test assays, one control) are performed using stepwise dilutions of test compound. The control assay has no test compound and consists of reaction buffer at final concentration (100 mM Tris, 4 mM EGTA, 4 mM EDTA, pH 7.0). The test assays include 0.01 μM test compound, 0.1 μM test compound, 1 μM test compound, 10 μM test compound and 100 μM test compound, respectively.

The reactions proceed at 37° C. for 1 minute. After reaction time has elapsed, the reaction may be terminated by addition of 100 μl of butanol. Reaction products in the butanol layer are resolved by TLC prior to quantification by scintillation spectrometry.

I claim:

1. A method of identifying compounds that modulate the activity of myocardial calcium-independent phospholipase $A_2$ comprising the steps of:
   a) performing a test assay comprising:
   i) combining myocardial calcium-independent phospholipase $A_2$ 40 kDa catalytic subunit, 85 kDa phosphofructokinase isoform, adenosine triphosphate, a substrate and a test compound to form a reaction mixture, wherein apparent molecular weights are determined by electrophoresis using 10% sodium dodecyl sulfate polyacrylamide gels;
   ii) maintaining said reaction mixture for a reaction time sufficient to allow myocardial calcium-independent phospholipase $A_2$ to process said substrate;
   iii) determining myocardial calcium-independent phospholipase $A_2$ activity; and
   b) comparing said activity to activity that results in a control assay which does not include said test compound.

2. The method of claim 1 wherein said substrate is selected from the group consisting of plasmenylcholine, plasmenylethanolamine, diacylphospholipids, alkylphospholids, triglycerides, diglycerides and monoglycerides.

3. The method of claim 1 wherein said substrate is labelled.

4. The method of claim 1 wherein said substrate is 16:0,[$^3$H]18:1 plasmenylcholine.

5. The method of claim 1 wherein said substrate is at a final concentration of about 0.1 nM to about 500 $\mu$M in said reaction mixture.

6. The method of claim 1 wherein said substrate is at a final concentration of about 10 $\mu$M in said reaction mixture.

7. The method of claim 1 wherein said adenosine triphosphate is at a final concentration of about 0.1 $\mu$M to about 100 $\mu$M in said reaction mixture.

8. The method of claim 1 wherein said test compound is at a final concentration of about 1 pM to about 100 $\mu$M in said reaction mixture.

9. The method of claim 1 wherein said test compound is at a final concentration of about 1 $\mu$M in said reaction mixture.

10. The method of claim 1 wherein said reaction mixture further comprises Tris, ethylene bis(oxyethylenenitrilo) tetraacetic acid and ethylene diaminetetraacetic acid at final concentrations of about 100 mM Tris, 4 mM ethylene bis(oxyethyleneitrilo) tetraacetic acid and 4 mM ethylene diaminetetraacetic acid, pH 7.0 in said reaction mixture.

11. The method of claim 1 wherein said reaction mixture is maintained for about 10 seconds to about 30 minutes at about 5° C. to about 37° C.

12. The method of claim 1 wherein said reaction mixture is maintained for about 1 minute at about 37° C.

13. The method of claim 1 wherein said myocardial calcium-independent phospholipase $A_2$ 40 kDa catalytic subunit and said 85 kDa phosphofructokinase isoform are in the form of a 400 kDa complex when combined with said adenosine tryphosphate, said substrate and said test compound.

14. The method of claim 1 wherein said myocardial calcium-independent phospholipase $A_2$ 40 kDa catalytic subunit and said 85 kDa phosphofructokinase isoform are in the form of a 400 kDa complex when combined with said adenosine tryphosphate, said substrate and said test compound; said reaction mixture contains about 1 pg to about 1 mg of said 400 kDa complex.

15. The method of claim 1 wherein said myocardial calcium-independent phospholipase $A_2$ 40 kDa catalytic subunit and said 85 kDa phosphofructokinase isoform are in the form of a 400 kDa complex when combined with said adenosine tryphosphate, said substrate and said test compound; said reaction mixture contains about 1 $\mu$g of said 400 kDa complex.

16. The method of claim 1 wherein said myocardial calcium-independent phospholipase $A_2$ 40 kDa catalytic subunit and said 85 kDa phosphofructokinase isoform are in the form of a 400 kDa complex when combined with said adenosine tryphosphate, said substrate and said test compound;
   i) said reaction mixture comprises: about 1 $\mu$g 400 kDa MCPA$_2$ complex; about 10 $\mu$M 16:0, [$^3$H] 18:1 plasmenylcholine; about 10 $\mu$M adenosine triphosphate; and, about 1 $\mu$M test compound; said reaction mixture further comprising 100 mM Tris, 4 mM ethylene bis(oxyethylenenitrilo) tetraacetic acid, 4 mM ethylene diaminetetraacetic acid, pH 7.0;
   ii) maintaining said reaction mixture at 37° C. for 1 minute;
   iii) after said reaction time has elapsed, adding 100 $\mu$l of butanol to said reaction mixture; and
   iv) determining myocardial calcium-independent phospholipase $A_2$ activity by resolving reaction products and quantifying reaction products by thin layer chromatography resolution followed by scintillation spectrometry.

17. The method of claim 1 wherein said myocardial calcium-independent phospholipase $A_2$ 40 kDa catalytic subunit is added to said reaction mixture as a purified protein and said 85 kDa phosphofructokinase isoform is added to said reaction mixture as a purified protein.

18. The method of claim 1 wherein said myocardial calcium-independent phospholipase $A_2$ 40 kDa catalytic subunit is added to said reaction mixture as a purified protein and said 85 kDa phosphofructokinase isoform is added to said reaction mixture as a purified protein; said reaction mixture contains about 1 pg to about 1 mg of said 40 kDa myocardial calcium-independent phospholipase $A_2$ catalytic subunit.

19. The method of claim 1 wherein said myocardial calcium-independent phospholipase $A_2$ 40 kDa catalytic subunit is added to said reaction mixture as a purified protein and said 85 kDa phosphofructokinase isoform is added to said reaction mixture as a purified protein; said reaction mixture contains about 20 ng of said 40 kDa myocardial calcium-independent phospholipase $A_2$ catalytic subunit.

20. The method of claim 1 wherein said myocardial calcium-independent phospholipase A$_2$ 40 kDa catalytic subunit is added to said reaction mixture as a purified protein and said 85 kDa phosphofructokinase isoform is added to said reaction mixture as a purified protein; said reaction mixture contains about 1 pg to about 1 mg of said 85 kDa phosphofructokinase isoform.

21. The method of claim 1 wherein said myocardial calcium-independent phospholipase A$_2$ 40 kDa catalytic subunit is added to said reaction mixture a purified protein and said 85 kDa phosphofructokinase isoform is added to said reaction mixture as a purified protein; said reaction mixture contains about 100 ng of said 85 kDa phosphofructokinase isoform.

22. The method of claim 1 wherein said myocardial calcium-independent phospholipase A$_2$ 40 kDa catalytic subunit is added to said reaction mixture as a purified protein and said 85 kDa phosphofructokinase isoform is added to said reaction mixture as a purified protein;
 i) said reaction mixture comprises: about 20 ng 40 kDa myocardial calcium-independent phospholipase A$_2$ catalytic subunit; about 100 ng 85 kDa phosphofructokinase isoform; about 10 μM 16:0, [$^3$H] 18:1 plasmenylcholine; about 10 μM adenosine triphosphate; and, about 1 μM test compound; said reaction mixture further comprising 100 mM Tris, 4 mM ethylene bis(oxyethylenenitrilo) tetraacetic acid, 4 mM ethylene diaminetetraacetic acid, pH 7.0;
 ii) maintaining said reaction mixture at 37° C. for 1 minute;
 iii) after said reaction time has elapsed, adding 100 μl of butanol to said reaction mixture; and
 iv) determining myocardial calcium-independent phospholipase A$_2$ activity by resolvig reaction products and by quantifying reaction products by thin layer chromatography resolution followed by scintillation spectrometry.

23. An isolated and purified 85 kDa phosphofructokinase isoform, wherein apparent molecular weight is determined by electrophoresis using 10% sodium dodecyl sulfate polyacrylamide gels.

* * * * *